(12) United States Patent
Deupree

(10) Patent No.: US 8,460,418 B2
(45) Date of Patent: Jun. 11, 2013

(54) HYDROPHOBIC FILTER ASSEMBLY FOR BIOPSY SYSTEM

(75) Inventor: David A. Deupree, Mason, OH (US)

(73) Assignee: Devicor Medical Products, Inc., Cincinnati, OH (US)

( * ) Notice: Subject to any disclaimer, the term of this patent is extended or adjusted under 35 U.S.C. 154(b) by 639 days.

(21) Appl. No.: 12/707,698

(22) Filed: Feb. 18, 2010

(65) Prior Publication Data

US 2011/0201963 A1 Aug. 18, 2011

(51) Int. Cl.
*B01D 46/00* (2006.01)

(52) U.S. Cl.
USPC ............... 55/385.1; 600/562; 600/564

(58) Field of Classification Search
USPC .... 55/385.1, 485, 486, 522, 524, 527; 428/36.1, 428/246, 284; 604/23, 24, 25, 26, 27, 28, 604/30, 31, 32, 33, 34, 35, 41
See application file for complete search history.

(56) References Cited

U.S. PATENT DOCUMENTS

| | | | |
|---|---|---|---|
| 5,526,822 A | | 6/1996 | Burbank et al. |
| 5,647,881 A * | | 7/1997 | Zhang et al. ............ 55/382 |
| 6,086,544 A | | 7/2000 | Hibner et al. |
| 6,576,033 B1 * | | 6/2003 | Booth .................. 55/485 |
| 6,585,791 B1 * | | 7/2003 | Garito et al. .......... 55/385.1 |
| 6,626,849 B2 | | 9/2003 | Huitema et al. |
| 6,746,504 B2 * | | 6/2004 | Booth .................. 55/485 |
| 7,442,171 B2 | | 10/2008 | Stephens et al. |
| 8,070,862 B2 * | | 12/2011 | Woo et al. ................ 96/69 |
| 2006/0074345 A1 | | 4/2006 | Hibner |
| 2007/0032742 A1 | | 2/2007 | Monson et al. |
| 2008/0214955 A1 | | 9/2008 | Speeg et al. |
| 2008/0228103 A1 | | 9/2008 | Ritchie et al. |
| 2009/0171242 A1 | | 7/2009 | Hibner |

OTHER PUBLICATIONS

U.S. Appl. No. 12/335,578, filed Dec. 16, 2008, Parihar et al.
U.S. Appl. No. 12/337,814, filed Dec. 18, 2008, Parihar et al.
U.S. Appl. No. 12/337,942, filed Dec. 18, 2008, Parihar et al.
U.S. Appl. No. 12/483,305, filed Jun. 12, 2009, Hibner et al.

* cited by examiner

*Primary Examiner* — Duane Smith
*Assistant Examiner* — Minh-Chau Pham
(74) *Attorney, Agent, or Firm* — Frost Brown Todd LLC

(57) ABSTRACT

A filter assembly has an outer member and an inner member. The outer member is configured to allow a vacuum to be communicated through the outer member. The outer member comprises hydrophobic material and an interior cavity. The hydrophobic material is configured to substantially repel fluids at atmospheric pressure. At least a portion of the inner member is positioned within the interior cavity of the outer member. The inner member comprises occluding media configured to absorb fluids both at atmospheric pressure and when a vacuum is being communicated through the inner member. The filter assembly may be incorporated within a vacuum canister to be used in conjunction with a biopsy device as part of a biopsy system, although other suitable applications will be apparent to those of ordinary skill in the art in view of the teachings herein.

20 Claims, 17 Drawing Sheets

HYDROPHOBIC FILTER ASSEMBLY FOR BIOPSY SYSTEM

BACKGROUND

Biopsy samples have been obtained in a variety of ways in various medical procedures using a variety of devices. Biopsy devices may be used under stereotactic guidance, ultrasound guidance, MRI guidance, PEM guidance, BSGI guidance, or otherwise. For instance, some biopsy devices may be fully operable by a user using a single hand, and with a single insertion, to capture one or more biopsy samples from a patient. In addition, some biopsy devices may be tethered to a vacuum module and/or control module, such as for communication of fluids (e.g., pressurized air, saline, atmospheric air, vacuum, etc.), for communication of power, and/or for communication of commands and the like. Other biopsy devices may be fully or at least partially operable without being tethered or otherwise connected with another device.

Merely exemplary biopsy devices are disclosed in U.S. Pat. No. 5,526,822, entitled "Method and Apparatus for Automated Biopsy and Collection of Soft Tissue," issued Jun. 18, 1996; U.S. Pat. No. 6,086,544, entitled "Control Apparatus for an Automated Surgical Biopsy Device," issued Jul. 11, 2000; U.S. Pub. No. 2003/0109803, entitled "MRI Compatible Surgical Biopsy Device," published Jun. 12, 2003; U.S. Pub. No. 2006/0074345, entitled "Biopsy Apparatus and Method," published Apr. 6, 2006; U.S. Pub. No. 2007/0118048, entitled "Remote Thumbwheel for a Surgical Biopsy Device," published May 24, 2007; U.S. Pub. No. 2008/0214955, entitled "Presentation of Biopsy Sample by Biopsy Device," published Sep. 4, 2008; U.S. Pub. No. 2009/0171242, entitled "Clutch and Valving System for Tetherless Biopsy Device," published Jul. 2, 2009; U.S. Non-Provisional patent application Ser. No. 12/335,578, entitled "Hand Actuated Tetherless Biopsy Device with Pistol Grip," filed Dec. 16, 2008; U.S. Non-Provisional patent application Ser. No. 12/337,942, entitled "Biopsy Device with Central Thumbwheel," filed Dec. 18, 2008; and U.S. Non-Provisional patent application Ser. No. 12/483,305, entitled "Tetherless Biopsy Device with Reusable Portion," filed Jun. 12, 2009. The disclosure of each of the above-cited U.S. Patents, U.S. Patent Application Publications, and U.S. Non-Provisional Patent Applications is incorporated by reference herein.

While several systems and methods have been made and used for obtaining a biopsy sample, it is believed that no one prior to the inventor(s) has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
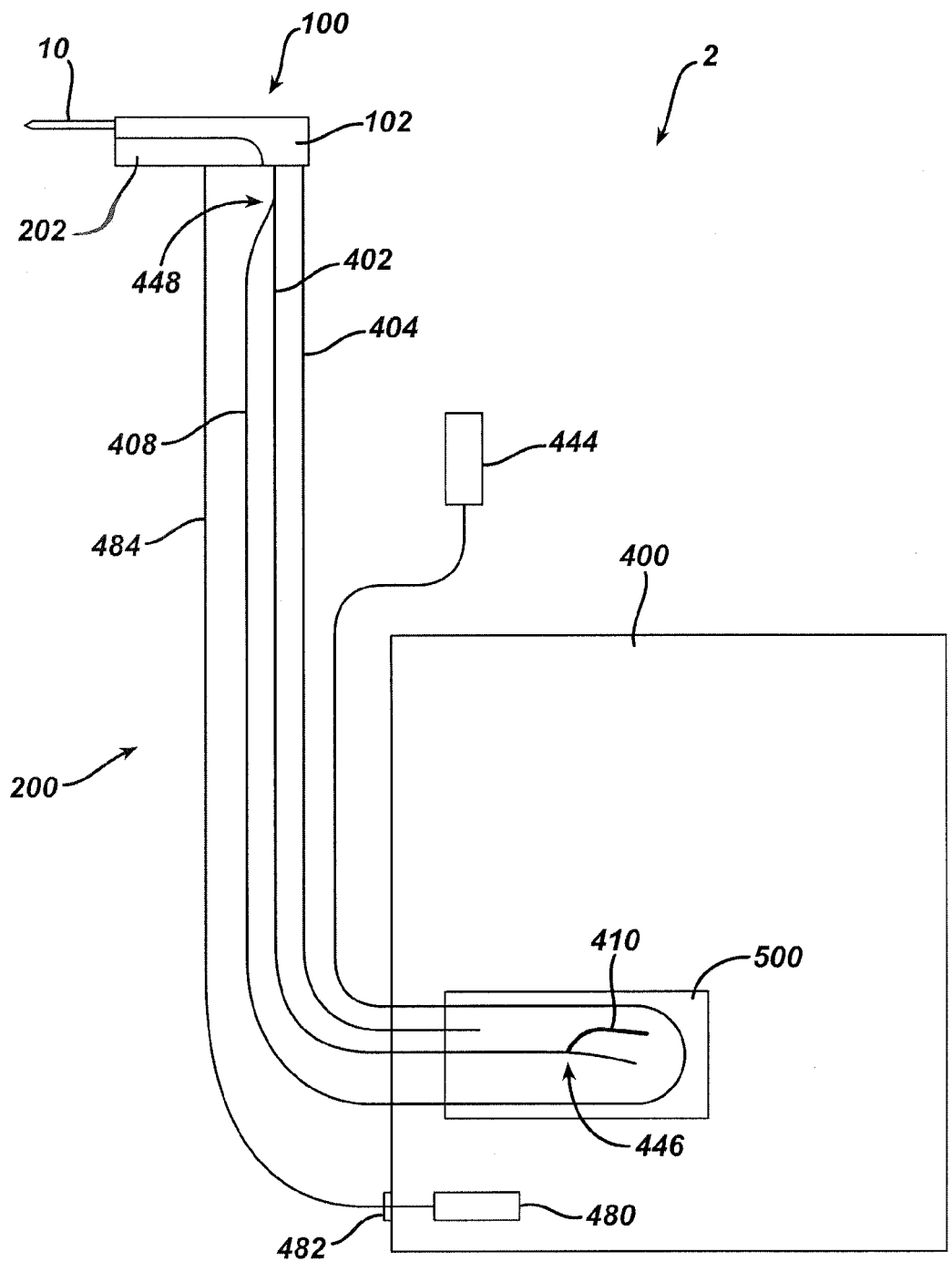
FIG. 1 depicts a schematic view of an exemplary biopsy system.
Figure 2:
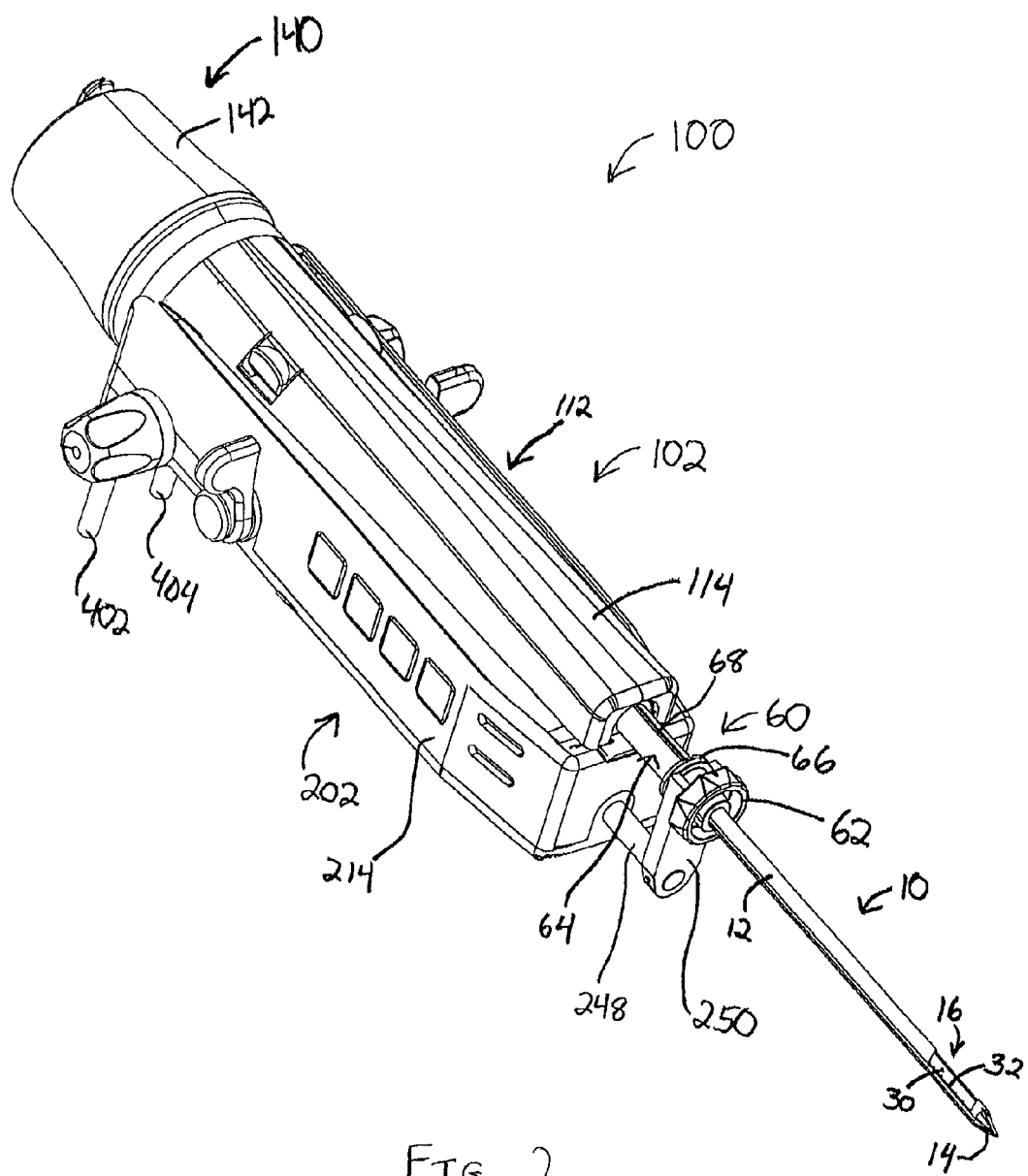
FIG. 2 depicts a perspective view of an exemplary assembled biopsy device, for use in a stereotactic setting.
Figure 3:
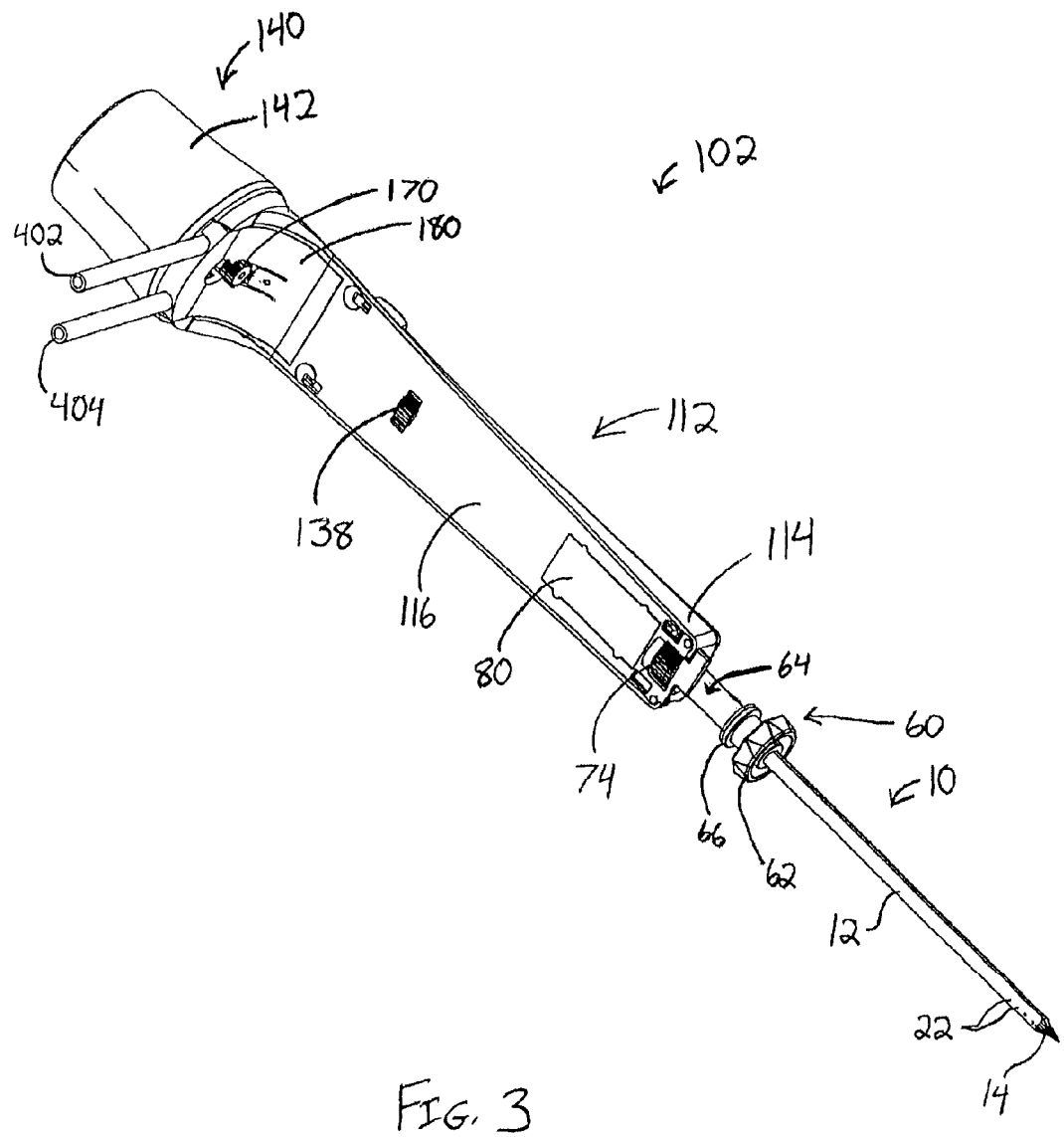
FIG. 3 depicts a bottom perspective view of a probe portion of the biopsy device of FIG. 2.

As shown in FIG. 1, an exemplary biopsy system (2) includes a biopsy device (100) and a vacuum control module (400). Conduits (200) provide communication of power (e.g., electrical, pneumatic, etc.), control signals, saline, vacuum, and venting from vacuum control module (400) to biopsy device (100). As shown in FIGS. 2-3, biopsy device (100) comprises a probe (102) and a holster (202). In some embodiments, biopsy device (100) is configurable and usable in accordance with the teachings of U.S. Pub. No. 2008/0228103, entitled "Vacuum Timing Algorithm for Biopsy Device," published Sep. 18, 2008, the disclosure of which is incorporated by reference herein. As will be described in greater detail below, probe (102) is separable from holster (202) in the present example, though other suitable structural and functional relationships between probe (102) and holster (202) will be apparent to those of ordinary skill in the art in view of the teachings herein.

In the present example, biopsy device (100) is configured for use in a stereotactic guidance setting. It will be appreciated that in other versions the biopsy device may be configured for use in other settings, including but not limited to an ultrasound guidance setting. An exemplary biopsy device configured for use in an ultrasound setting is described in U.S. Pub. No. 2008/0228103, entitled "Vacuum Timing Algorithm for Biopsy Device," published Sep. 18, 2008, the disclosure of which is incorporated by reference herein. Other suitable settings in which biopsy device (100) may be used may include but need not be limited to those in which biopsy device (100) is used under MRI guidance, PEM guidance, BSGI guidance, or otherwise.

I. Exemplary Probe

Figure 4:
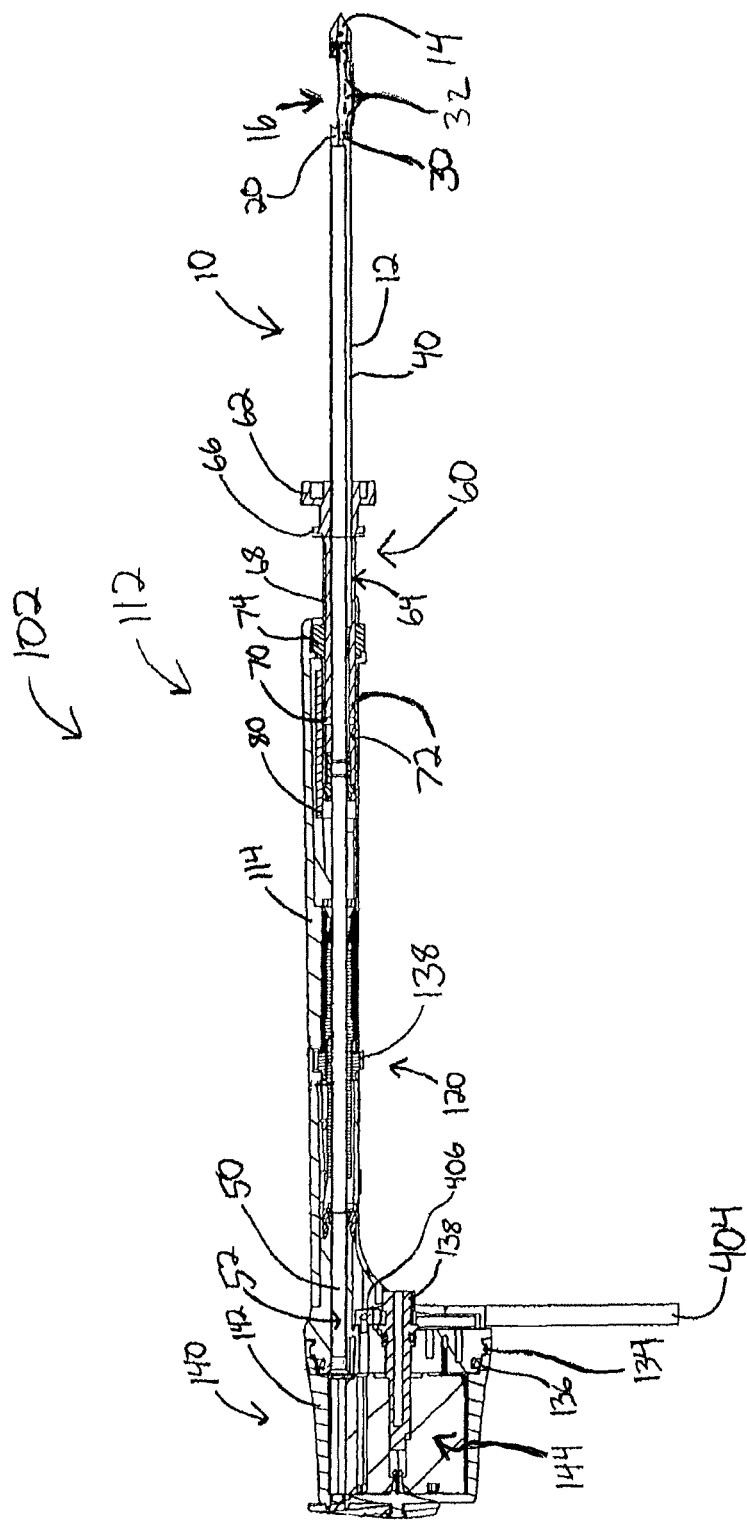
FIG. 4 depicts a lateral cross-sectional view of the probe portion of FIG. 3, taken along a longitudinal plane.

In some versions, probe (102) is configured and operable in accordance with the teachings of U.S. Pub. No. 2008/0228103, entitled "Vacuum Timing Algorithm for Biopsy Device," published Sep. 18, 2008, the disclosure of which is incorporated by reference herein. In some other versions, probe (102) is configured and operable in accordance with the teachings of U.S. Non-Provisional patent application Ser. No. 12/337,942, entitled "Biopsy Device with Central Thumbwheel," filed Dec. 18, 2008, the disclosure of which is incorporated by reference herein. As shown in FIGS. 2-4, probe (102) of the present example comprises a needle portion (10) and a body portion (112). Body portion (112) comprises a cover member (114) and a base member (116). A tissue sample holder (140) is removably secured to base member (116). As will be described in greater detail below, a pair of tubes (402, 404) are coupled with probe (102).

Needle portion (10) of the present example comprises an outer cannula (12) having a tissue piercing tip (14) and a transverse tissue receiving aperture (16) located proximally from the tissue piercing tip (14). Tissue piercing tip (14) is configured to penetrate tissue without requiring a high amount of force, and without requiring an opening to be preformed in the tissue prior to insertion of tip (14). The interior of outer cannula (12) of the present example defines a cannula lumen (20) and a vacuum lumen (40), with a wall (30) separating the cannula lumen (20) from the vacuum lumen (40). A plurality of external openings (22) are formed in outer cannula (12), and are in fluid communication with vacuum lumen (40). Such external openings (22) may be configured in accordance with the teachings of U.S. Pub. No. 2007/0032742, entitled "Biopsy Device with Vacuum Assisted Bleeding Control," published Feb. 8, 2007, the disclosure of which is incorporated by reference herein. In the present example, a plurality of transverse openings (32) are formed through wall (30) to provide fluid communication between cannula lumen (20) and vacuum lumen (40). As will be described in greater detail below, vacuum, saline, and/or pressurized air may be communicated from vacuum lumen (40) to cannula lumen (20) via transverse openings (32).

A hollow cutter (50) is disposed within cannula lumen (20). The interior of cutter (50) defines a cutter lumen (52), such that fluid and tissue may be communicated through cutter (50) via cutter lumen (52). As will be described in greater detail below, cutter (50) is configured to rotate within cannula lumen (20) and translate axially within cannula lumen (20). In particular, cutter (50) is configured to sever a biopsy sample from tissue protruding through transverse aperture (16) of outer cannula (12). As will also be described in greater detail below, cutter (50) is further configured to permit severed tissue samples to be communicated proximally through cutter lumen (52). Merely illustrative examples of such severing and proximal communication are described in U.S. Pat. No. 5,526,822, entitled "Method and Apparatus for Automated Biopsy and Collection of Soft Tissue," issued Jun. 18, 1996, the disclosure of which is incorporated by reference herein, though any other suitable structures or techniques may be used for severing and/or communicating tissue samples within a biopsy system (2).

In some versions, needle portion (10) and its components and/or cutter (50) and its components are configured and operable in accordance with the teachings of U.S. Pub. No. 2008/0228103, entitled "Vacuum Timing Algorithm for Biopsy Device," published Sep. 18, 2008, the disclosure of which is incorporated by reference herein. In some other versions, needle portion (10) and its components and/or cutter (50) and associated components are configured and operable in accordance with the teachings of U.S. Non-Provisional patent application Ser. No. 12/337,942, entitled "Biopsy Device with Central Thumbwheel," filed Dec. 18, 2008, the disclosure of which is incorporated by reference herein. Still other ways in which needle portion (10) and cutter (50) may be formed, including alternative techniques, materials, and configurations, will be apparent to those of ordinary skill in the art in view of the teachings herein.

As shown in FIGS. 2-4, a needle hub (60) is secured to outer cannula (12), and comprises a thumbwheel (62) and a sleeve portion (64) extending proximally from thumbwheel (62). Sleeve portion (64) comprises an annular projection (66), a longitudinal slot (68), and a transverse opening (70), which is formed near the proximal end of sleeve portion (64). One or more additional transverse openings (70) (e.g., diametrically opposed transverse openings (70)) may also be provided in sleeve portion (64). A pair of o-rings (72) are positioned such that one o-ring (72) is proximal to transverse opening (70) and another o-ring (72) is distal to transverse opening (70). Transverse opening (70) is in fluid communication with the interior defined by needle hub (60), which is also in fluid communication with vacuum lumen (40) of outer cannula (12).

As shown in FIG. 4, a needle manifold (80) is provided about sleeve portion (64). Needle manifold (80) is fixed relative to base member (116) in this example. Needle manifold (80) is in fluid communication with tube (402), such that tube (402) may communicate saline, a vacuum, atmospheric air, and/or pressurized air, etc., to needle manifold (80), as will be described in greater detail below. Needle manifold (80) is further in fluid communication with the interior of sleeve portion (64), via transverse opening (70). O-rings (64) are configured to maintain a fluid seal between needle manifold (80) and sleeve portion (64), even as sleeve portion (64) translates longitudinally relative to needle manifold (80), such as during firing of needle (10); and even during rotation of sleeve portion (64) about its longitudinal axis. Such rotation is effected through interaction between gear (74) of needle hub (60) and gear (206) of holster (202) when probe (102) and holster (202) are coupled together. A seal (not shown) is also provided at the proximal end of sleeve portion (64), at the interface between sleeve portion (64) and cutter (50). Needle manifold (80), sleeve portion (64), and outer cannula (12) are thus configured and arranged such that saline, a vacuum, atmospheric air, and/or pressurized air, etc. that is communicated via tube (402) to needle manifold (80) will be communicated to vacuum lumen (40) via transverse opening (70). Of course, any other suitable structures or arrangements may be used to communicate saline, a vacuum, atmospheric air, and/or pressurized air, etc. from tube (402) to vacuum lumen (40).

In some versions, needle hub (60) and associated components and/or needle manifold (80) and associated components are configured and operable in accordance with the teachings in U.S. Pub. No. 2008/0228103, entitled "Vacuum Timing Algorithm for Biopsy Device," published Sep. 18, 2008, the disclosure of which is incorporated by reference herein. In some other versions, needle hub (60) and associated components and/or needle manifold (80) and associated components are configured and operable in accordance with the teachings of U.S. Non-Provisional patent application Ser. No. 12/337,942, entitled "Biopsy Device with Central Thumbwheel," filed Dec. 18, 2008, the disclosure of which is incorporated by reference herein. Still other ways in which needle hub (60)

and needle manifold (80) may be formed, including alternative techniques, materials, and configurations, will be apparent to those of ordinary skill in the art in view of the teachings herein.

In the present example, and as shown in FIG. 4, body portion (112) of probe (102) comprises a cutter rotation and translation mechanism (120), which is operable to rotate and translate cutter (50) within outer cannula (12). Such rotation and translation is effected through interaction between gear (138) of probe (102) and gear (208) of holster (202) when probe (102) and holster (202) are coupled together. In some versions, cutter rotation and translation mechanism (120) is configured and operable in accordance with any of the teachings in U.S. Pub. No. 2008/0228103, entitled "Vacuum Timing Algorithm for Biopsy Device," published Sep. 18, 2008, the disclosure of which is incorporated by reference herein. In some other versions, cutter rotation and translation mechanism (120) and associated components are configured and operable in accordance with the teachings of U.S. Non-Provisional patent application Ser. No. 12/337,942, entitled "Biopsy Device with Central Thumbwheel," filed Dec. 18, 2008, the disclosure of which is incorporated by reference herein. Still other ways in which cutter rotation and translation mechanism (120) may be formed, including alternative techniques, materials, and configurations, will be apparent to those of ordinary skill in the art in view of the teachings herein.

As shown in FIGS. 2-4, a tissue sample holder (140) is provided at the end of body portion (112) of probe (102). Tissue sample holder (140) comprises a cup (142), a manifold (144), and a plurality of trays (not shown). Tissue sample holder (140) further comprises a central recess, a plurality of longitudinal passages, a plurality of chambers, and a plurality of radial passages configured to provide fluid communication within tissue sample holder (140). In the illustrated example, cup (142) is configured to engage bayonets (134) of base member (116), such that cup (142) may be removed from or secured to base member (116) upon sufficient rotation of cup (142) relative to base member (116). In addition, an o-ring (136) is provided about base member (116) to provide a seal between base member (116) and cup (142). Of course, any other suitable structures may be used to provide engagement of cup (142) with base member (116) and/or to provide a seal between base member (116) and cup (142).

Manifold (144) of the present example is configured to rotate relative to base member (116). Such rotation is effected through interaction between gear (170) of tissue sample holder (140) and gear (210) of holster (202) when probe (102) and holster (202) are coupled together. Manifold (144) of the present example is further configured such that each longitudinal passage may be selectively aligned with a port (406) that is in fluid communication with tube (404). Such alignment of a longitudinal passage and port (406) will place the aligned longitudinal passage in fluid communication with tube (404), such that induction of a vacuum within tube (404) will effect induction of a vacuum within a longitudinal passage, as well as within the chamber (not shown) associated with that longitudinal passage. In addition, manifold (144) and trays (not shown) of the present example are configured such that each chamber may be selectively placed in fluid communication with cutter lumen (52). It will therefore be appreciated that a vacuum in tube (404) may induce a vacuum in cutter lumen (52), with the vacuum being communicated via port (406), an associated longitudinal passage, an associated radial passage, an associated pair of openings, an associated chamber, an associated set of openings, and an associated chamber. Of course, there are a variety of other ways in which a vacuum may be induced within a cutter lumen (52), and any other suitable structures or techniques may be used. Furthermore, pressurized air, a liquid (e.g., saline), or any other fluid may be communicated in either direction through the above-mentioned components in lieu of or in addition to a vacuum being induced therein.

In some versions, tissue sample holder (140) and its components are configured and operable in accordance with the teachings of U.S. Pub. No. 2008/0228103, entitled "Vacuum Timing Algorithm for Biopsy Device," published Sep. 18, 2008, the disclosure of which is incorporated by reference herein. In some other versions, tissue sample holder (140) and associated components are configured and operable in accordance with the teachings of U.S. Non-Provisional patent application Ser. No. 12/337,942, entitled "Biopsy Device with Central Thumbwheel," filed Dec. 18, 2008, the disclosure of which is incorporated by reference herein. Still other ways in which tissue sample holder (140) may be formed, including alternative techniques, materials, and configurations, will be apparent to those of ordinary skill in the art in view of the teachings herein.

II. Exemplary Holster

Figure 5:
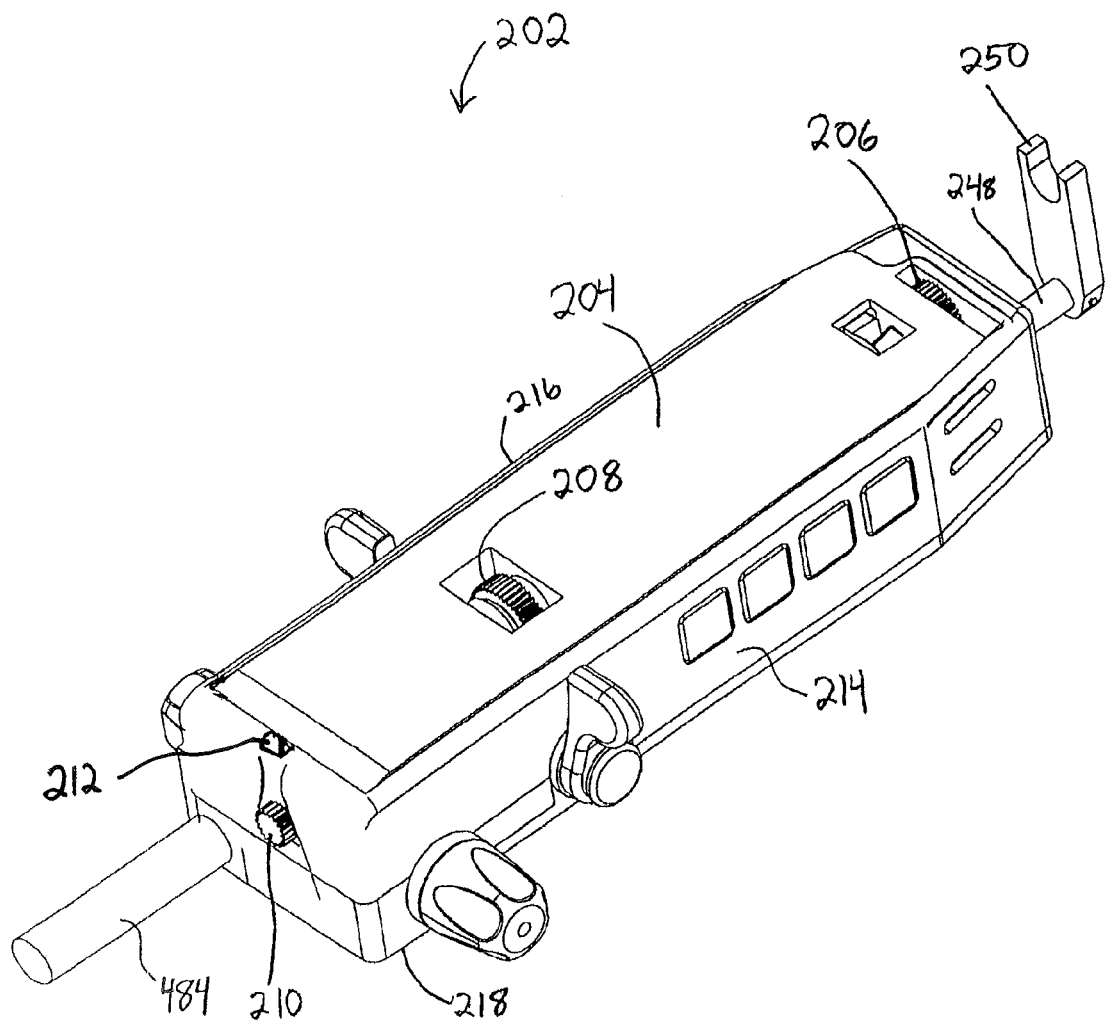
FIG. 5 depicts a perspective view of a holster portion of the biopsy device of FIG. 2.

As shown in FIGS. 2 and 5, holster (202) of the present example comprises a top cover (204), through which a portion of each of gears (206, 208, 210) is exposed, side panels (214, 216), and a base member (218). Boss (212) is provided on top cover (204), and is configured to disengage pawl portion (182) from gear (170) when biopsy probe (102) is coupled with holster (202). In addition, a user interface may be provided on each side panel (214, 216). Holster (202) of this example further comprises a needle rotation mechanism (not shown), which is operable to rotate gear (206) to rotate needle portion (10); a needle firing mechanism (not shown), which is operable to translate shaft (248) and fork (250) to translate needle portion (10); a cutter drive mechanism (not shown), which is operable to rotate gear (208) to simultaneously rotate and translate cutter (50); and a tissue holder rotation mechanism (not shown), which is operable to rotate gear (210) to rotate manifold (144). It should be understood that one or more of the needle rotation mechanism, the needle firing mechanism, the cutter drive mechanism, and/or the tissue holder rotation mechanism may be configured and operable in accordance with the teachings of U.S. Pub. No. 2008/0228103, entitled "Vacuum Timing Algorithm for Biopsy Device," published Sep. 18, 2008, the disclosure of which is incorporated by reference herein. Alternatively, any or all of these mechanisms may be configured and operable in accordance with the teachings of U.S. Non-Provisional patent application Ser. No. 12/337,942, entitled "Biopsy Device with Central Thumbwheel," filed Dec. 18, 2008, the disclosure of which is incorporated by reference herein. Other suitable configurations, features, and variations of a needle rotation mechanism, needle firing mechanism, cutter drive mechanism, and tissue holder rotation mechanism will be apparent to those of ordinary skill in the art in view of the teachings herein.

As noted above, holster (202) of the present example is configured to be coupled with biopsy probe (102) to provide assembled biopsy device (100). In addition, holster (202) is configured to be mounted to a table, fixture, or other device, such as for use in a stereotactic or X-ray setting. However, it will be appreciated in view of the disclosure herein that holster (202) may be used in a variety of other settings and combinations. In some versions, holster (202) and associated components are configured and operable in accordance with the teachings of U.S. Pub. No. 2008/0228103, entitled "Vacuum Timing Algorithm for Biopsy Device," published Sep. 18, 2008, the disclosure of which is incorporated by reference herein. In some other versions, holster (202) and associated components are configured and operable in accordance with the teachings of U.S. Non-Provisional patent application Ser. No. 12/337,942, entitled "Biopsy Device with Central Thumbwheel," filed Dec. 18, 2008, the disclosure of which is incorporated by reference herein. Still other ways in which holster (202) may be formed, including alternative techniques, materials, and configurations, will be apparent to those of ordinary skill in the art in view of the teachings herein.

III. Exemplary Vacuum Control Module and Canister

Figure 6:
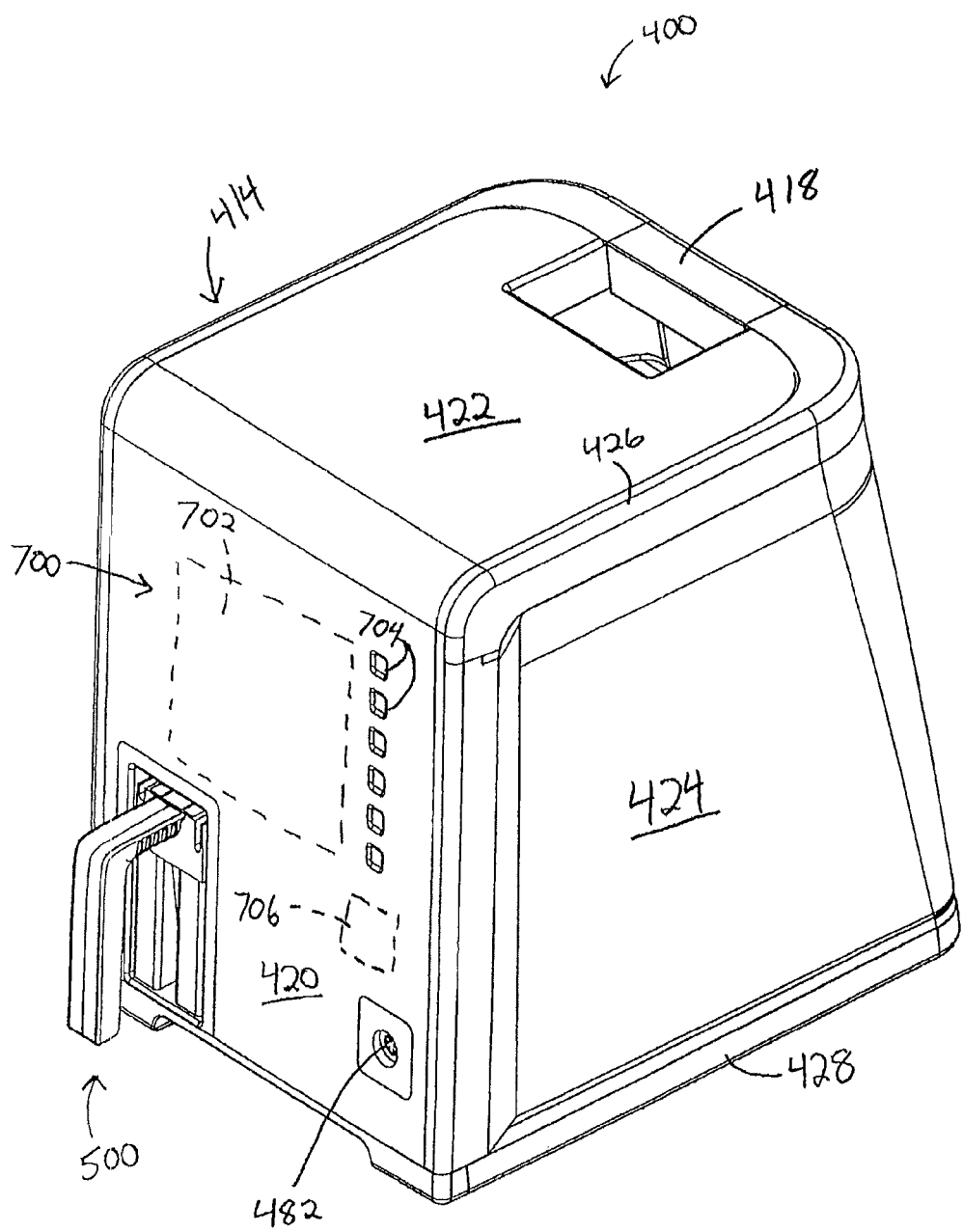
FIG. 6 depicts a perspective view of an exemplary vacuum control module and exemplary vacuum canister.
Figure 7:
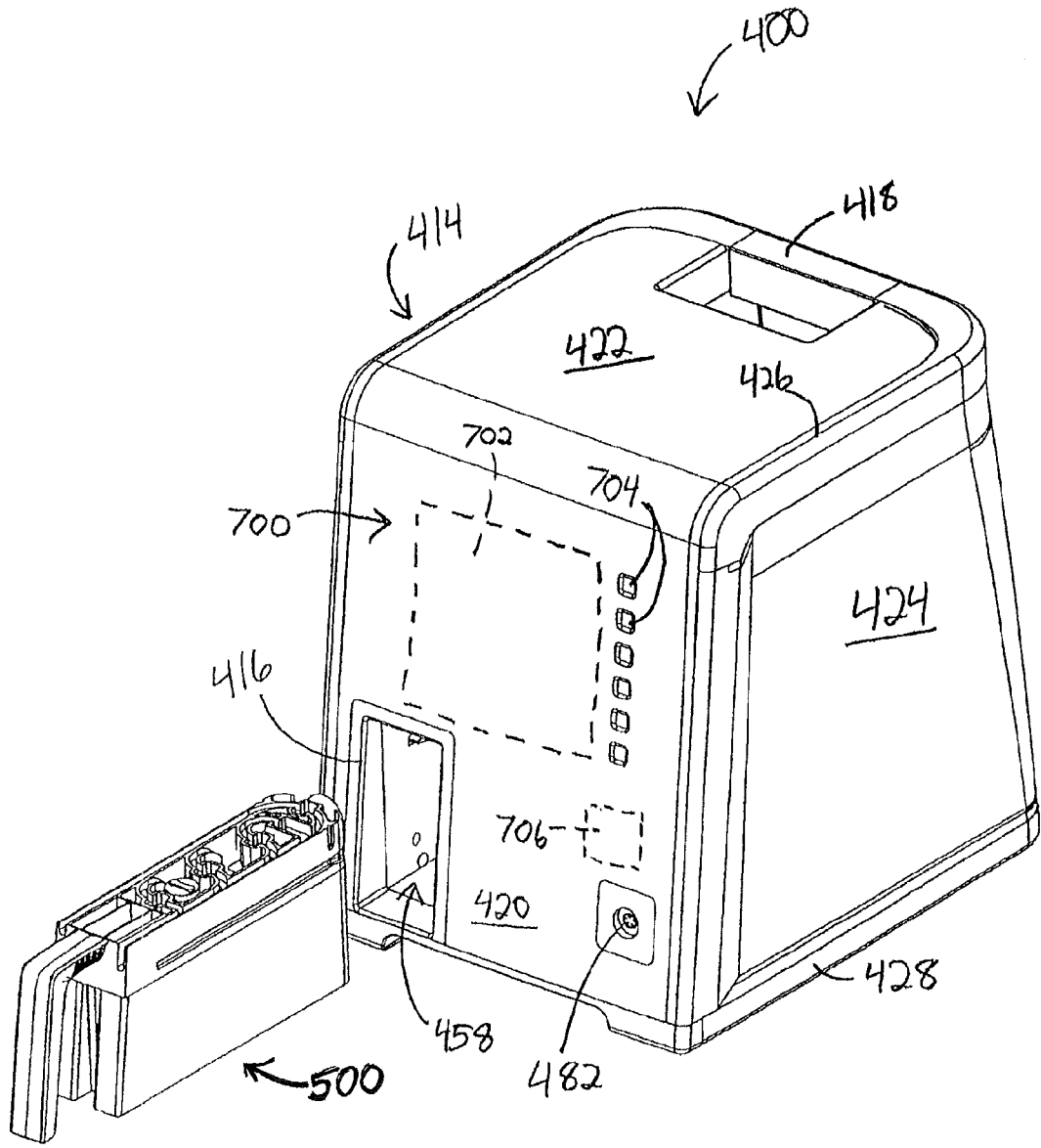
FIG. 7 depicts the vacuum control module of FIG. 6 with the vacuum canister of FIG. 8 separated therefrom.
Figure 8:
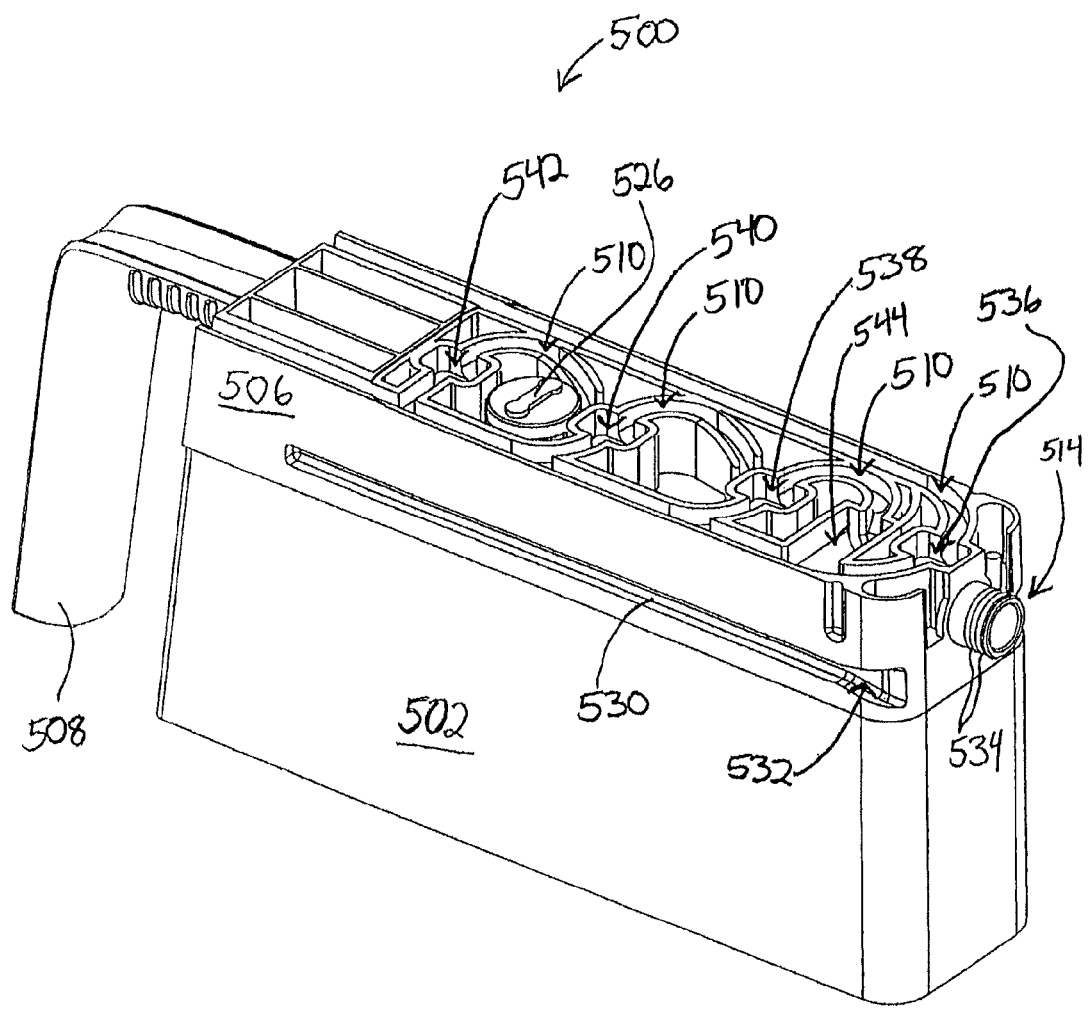
FIG. 8 depicts a perspective view of the vacuum canister of FIG. 6.
Figure 9:
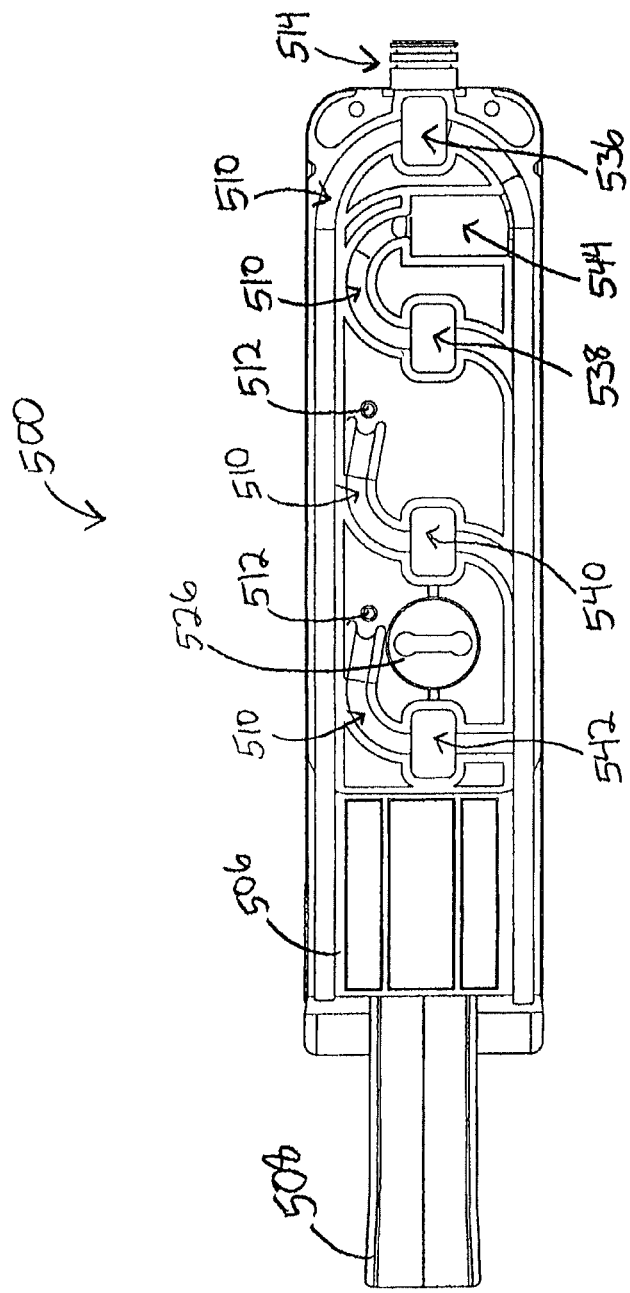
FIG. 9 depicts a top view of the vacuum canister of FIG. 6.

FIGS. 6-7 show an exemplary vacuum control module (400) and an exemplary vacuum canister (500). As shown, vacuum canister (500) is configured to be inserted into vacuum control module (400). As will be described in greater detail below, vacuum control module (400) is operable to induce a vacuum through vacuum canister (500), and such a vacuum may be communicated to biopsy probe (102) as described above. Furthermore, vacuum canister (500) is operable to collect fluids that are communicated from biopsy probe (102) during use of biopsy probe (102). Vacuum canister (500) may thus be regarded as providing a fluid interface between biopsy probe (102) and vacuum control module (400). In some versions, vacuum control module (400), vacuum canister (500), and associated components are configured and operable in accordance with the teachings of U.S. Pub. No. 2008/0228103, entitled "Vacuum Timing Algorithm for Biopsy Device," published Sep. 18, 2008, the disclosure of which is incorporated by reference herein. Other suitable configurations will be apparent to those of ordinary skill in the art in view of the teachings herein.

A. Exemplary Vacuum Canister

As shown in FIGS. 8-11, vacuum canister (500) of the present example comprises a base portion (502), a lid portion (506), and a handle (508). Handle (508) is configured to be gripped by a user when user inserts vacuum canister (500) into vacuum control module (400) or withdraws vacuum canister (500) from vacuum control module (400). Base portion (502) is substantially hollow, and is configured to provide a reservoir (504) for collection of fluids (e.g., saline, blood, etc.) communicated from biopsy probe (102). Lid portion (506) has a plurality of trenches (510) formed therein. As will be described below, trenches (510) are configured to receive tubes (402, 404, 408, 410). A plurality of top ports (512) are formed on lid portion (506), and each top port (512) is configured have one of tubes (402, 404) coupled therewith. In particular, each top port (512) is configured to provide a path for fluid communication from a connected tube (402, 404) to the reservoir (504) defined by base portion (502). Accordingly, fluids (e.g., saline, blood, etc.) may be communicated from biopsy probe (102) during operation of biopsy device (100) and collected in reservoir (504). Lid portion (506) further comprises a vacuum port (514), which is configured to be placed in fluid communication with a vacuum source (412) in vacuum control module (400), as will be described in greater detail below. Vacuum port (514) includes a pair of o-rings (534) configured to provide a seal when engaged with a complementary vacuum port (462) as will be described in greater detail below. It will be appreciated in view of the teachings herein that, when vacuum source (412) is used to generate a vacuum, such a vacuum may be communicated to tubes (402, 404) via vacuum port (514), reservoir (504), and top ports (512). The vacuum may be further communicated to biopsy probe (102) via tubes (402, 404). Lid portion (506) also includes a vent recess (544), configured for venting the open end of a vent tube (410) to atmosphere.

Lid portion (506) of the present example also has a cap (526) that is removably secured to an access port (528). Cap (526) is configured to provide a seal of access port (528) during use of biopsy system (2). After biopsy system (2) has been used, and liquid is present in reservoir (504), cap (526) may be removed to gain access to reservoir (504). A user may empty liquid from reservoir (504) by pouring the liquid out of reservoir (504) via access port (528). Other suitable methods for removing liquid from reservoir (504) will be apparent to those of ordinary skill in the art in view of the teachings herein. Of course, like other components mentioned herein, cap (526) and access port (528) are merely optional, and may be varied, substituted, supplemented, or simply omitted altogether, as desired.

Figure 11:
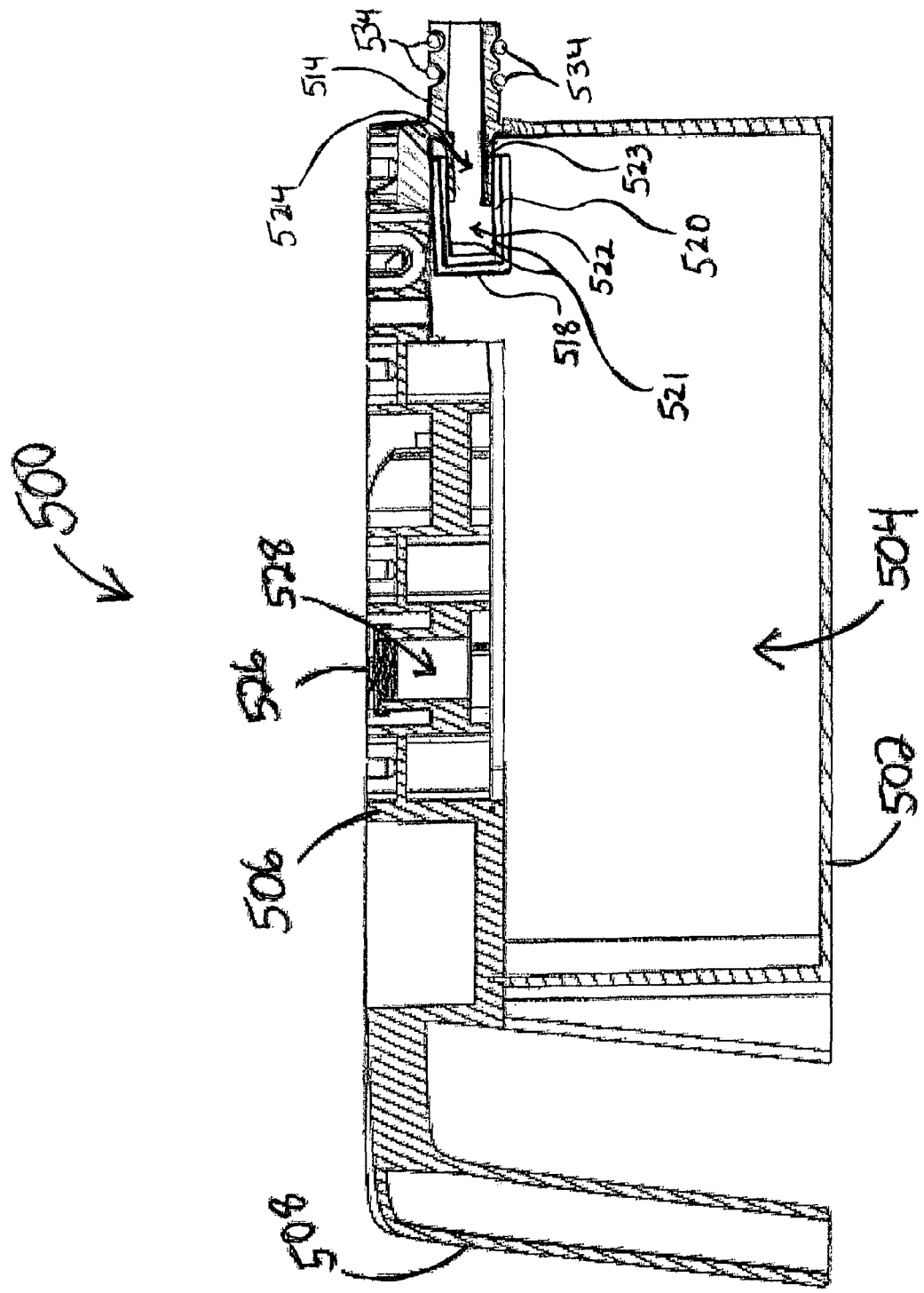
FIG. 11 depicts a cross-sectional view of the canister of FIG. 6, taken along a longitudinal plane.
Figure 12:
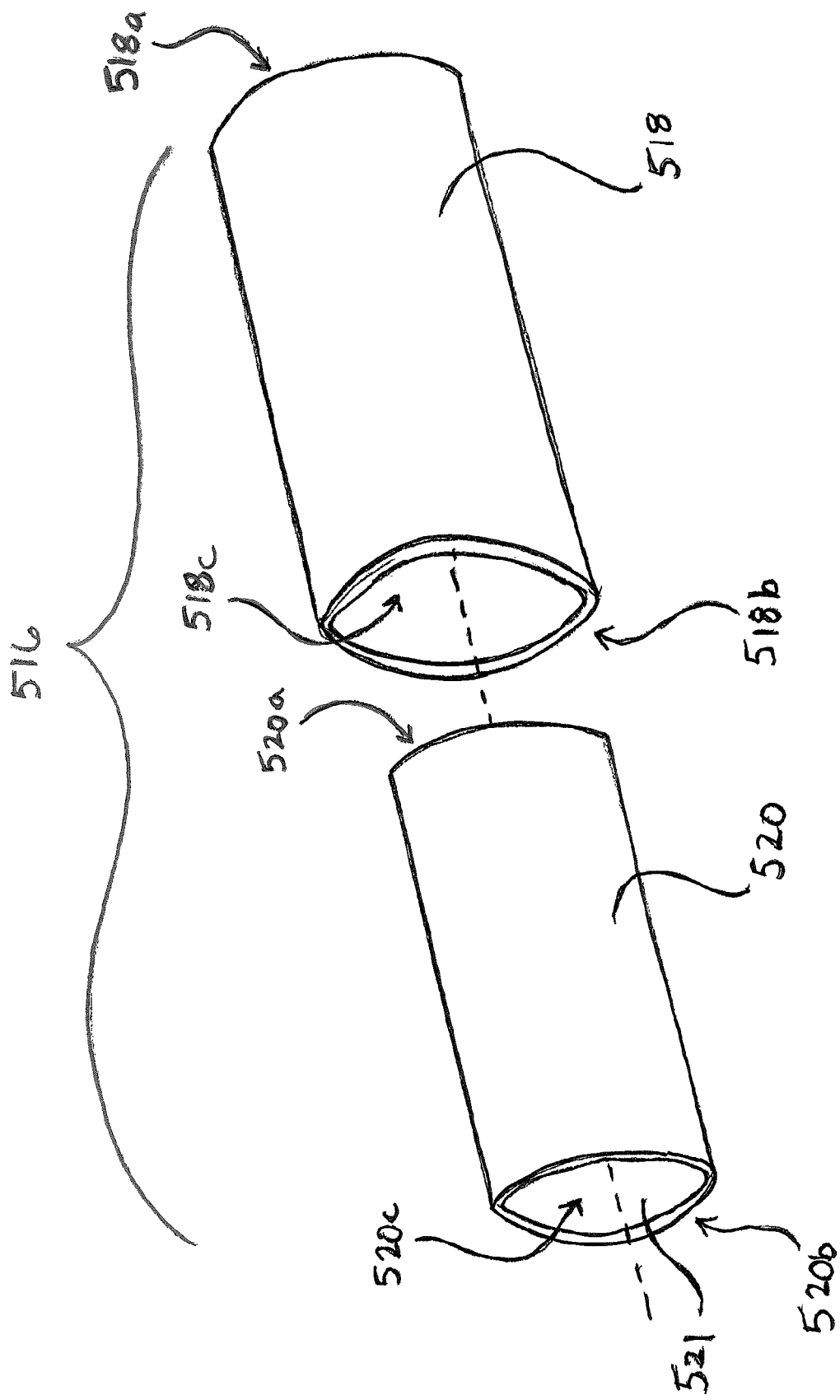
FIG. 12 depicts a perspective, exploded assembly view of an exemplary filter assembly.
Figure 17:
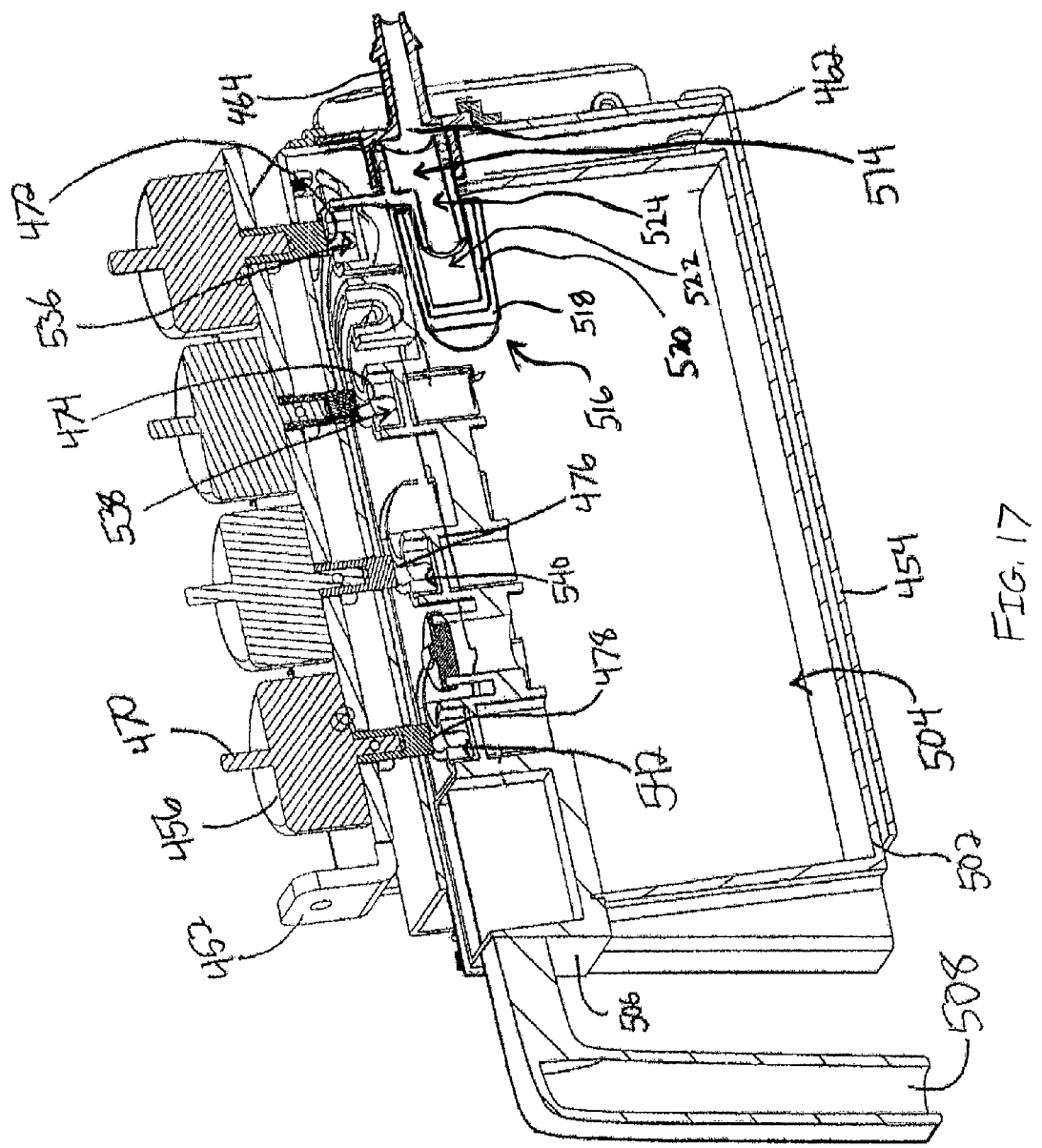
FIG. 17 depicts a cross-sectional view of the vacuum canister port assembly of FIG. 16 with the vacuum canister of FIG. 6 inserted therein.

As shown in FIGS. 11-12 and 17, a filter assembly (516) is positioned within reservoir (504) of vacuum canister (500). A conduit (524) is formed in lid portion (506), providing fluid communication from vacuum port (514) to filter assembly (516), and therefore, to reservoir (504). Filter assembly (516) of the present example is configured and positioned to substantially prevent fluids (e.g. blood, saline, etc.) collected within reservoir (504) from being communicated into vacuum source (412) via conduit (524) and vacuum port (514). In the present example, filter assembly (516) comprises an outer member or layer (518) and an inner member or layer (520).

Outer member (518) and inner member (520) of the present example are configured to allow a vacuum to be communicated from vacuum source (412) through filter assembly (516) and, ultimately, to tubes (402, 404) via vacuum port (514), conduit (524), reservoir (504), and ports (512). As shown, outer member (518) and inner member (520) each comprise hollow, cylindrical members having a closed end (518a, 520a) and an open end (518b, 520b) and forming a respective interior cavity (518c, 520c). In some other versions, inner member (520) comprises a solid, cylindrical member or plug. In the present example, inner member (520) is sized and shaped such that inner member (520) may be inserted into and received by the interior cavity (518c) formed by outer member (518). In particular, inner member (520) is inserted into interior cavity (518c) of outer member (518) such that the outer surface of inner member (520) abuts the inner surface of outer member (518). In some other versions, outer surface of inner member (520) may be spaced apart from inner surface of outer member (518). As shown, the interior cavity (522) of inner member (520) is in fluid communication with vacuum port (514) via conduit (524) formed in lid (506).

Outer member (518) and inner member (520) may be fixedly or releasably engaged with each other. In the present example, a two layered sintering process is used to fuse outer member (518) with inner member (520). Of course, any other suitable methods and techniques for joining outer member (518) and inner member (520) may be used. By way of example only, outer member (518) and inner member (520) may be sized and shaped to provide an interference fit between the two members. In yet another example, an adhesive may be utilized to engage outer member (518) attach outer member (518) and inner member (520). As another merely illustrative example, outer member (518) and inner member (520) may be joined together through heat staking, ultrasonic welding, and/or overmolding. Other suitable methods and devices for engaging outer member (518) and inner member (520) will be apparent to those of ordinary skill in the art. In the present example, lid portion (506) comprises an attachment member (523) or lip that defines part of conduit (524) and is configured to engage an interior surface (521) of inner member (520). Inner member (520) may be fixedly or releasably engaged with attachment member (523). By way of example only, inner member (520) may be affixed to attachment member (523) using an adhesive, interference fit, heat staking, ultrasonic welding, and/or overmolding. Alternatively, inner member (520) and attachment member (523) may comprise corresponding threads or tabs to provide selective engagement between inner member (520) and attachment member (523). Other suitable methods and devices for engagement between inner member (520) and attachment member (523) will be apparent to those of ordinary skill in the art in view of the teachings herein.

Outer member (518) and inner member (520) may possess different characteristics when exposed to fluids. By way of example only, outer member (518) may comprise a hydrophobic material configured to substantially repel fluids when there is no vacuum being communicated through outer member (518). Outer member (518) may thus provide a form of hydrophobic filter. However, outer member (518) may be configured such that outer member's (518) ability to repel fluids is diminished when a vacuum is communicated through outer member (518). Accordingly, outer member (518) may allow at least a small amount of fluid to soak or pass through outer member (518) when a vacuum is communicated through filter assembly (516) via conduit (524) and vacuum port (514). By way of example only, outer member (518) may comprise a breathable polyolefin material, such as a polyethylene material and/or a polypropylene material. Other suitable materials or combinations of materials that may be used to form outer member (518) will be apparent to those of ordinary skill in the art in view of the teachings herein.

Inner member (520) may comprise occluding media configured to absorb fluids both at atmospheric pressure and when a vacuum is being communicated through inner member (520). However, the ability of filter assembly (516) to communicate a vacuum may be diminished as inner member (520) absorbs fluids and gradually occludes. In other words, as a larger portion of inner member (520) is exposed to fluids and swells, the vacuum communicated through filter assembly (516) may be weakened. Inner member (520) may comprise a cellulosic media or any other suitable material. An exemplary filter using occluding media is incorporated within a suction canister produced by Porex Corporation of Fairburn, Ga. Such an occluding media may be used to form inner member (520). As another merely illustrative example, inner member (520) may comprise a breathable polyolefin material, such as a polyethylene material and/or a polypropylene material. Other suitable materials or combinations of materials that may be used to form inner member (520) will be apparent to those of ordinary skill in the art in view of the teachings herein. It should also be understood that outer member (518) and/or inner member may further comprise a variety of other materials, including but not limited to polyether ether ketone (PEEK), in addition to or in lieu of the materials described herein.

Accordingly, in the present example, when there is no vacuum being communicated through filter assembly (516) (e.g. when vacuum source (412) is not active, when canister (500) is removed from vacuum control module (400), etc.), outer member (518) repels substantially all fluids that come into contact with filter assembly (516) from within reservoir (504), thereby substantially preventing the fluids from reaching inner member (520) and/or conduit (524) and vacuum port (514). For instance, to the extent that the user needs to empty fluids from reservoir (504) of canister (500) during use of biopsy system (2), outer member (518) will substantially protect inner member (518) from any incidental splashing of fluids against filter assembly (516) that might occur during transport of canister (500) to a fluid dumping location. In other words, if fluids come into contact with filter assembly (516) when no vacuum is present, the amount of fluids ultimately reaching and occluding inner member (520) is decreased and the negative impact on the filter assembly's (516) ability to communicate a vacuum is also decreased as compared to a filter assembly consisting entirely of occluding media. Outer member (518) thus prevents premature wetting of inner member (520). In addition, when a vacuum is being communicated through filter assembly (516), fluids that contact filter assembly (516) and are able to pass through outer member (518) (due to the presence of a vacuum) are substantially absorbed by inner member (520) and, thus, are prevented from reaching conduit (524) and vacuum port (514).

In some settings, the amount of fluid that reaches inner member (520) during normal use of biopsy system (2) will not be great enough to cause inner member (520) to swell to the point that filter assembly (516) can no longer effectively communicate a vacuum. However, if a portion of inner member (520) absorbs enough fluids during use of biopsy system (2) to the point where filter assembly (516) can no longer effectively communicate a vacuum, the user may replace vacuum canister (500) with a new vacuum canister (500) that includes a new filter assembly (516) to restore the vacuum to full strength. In some other versions, a user may restore vacuum to full strength without replacing the entire canister (500). For example, some such versions, the user may remove vacuum canister (500) from vacuum control module (400), remove lid portion (506), and replace the used filter assembly (516) with a new filter assembly (516). In some other versions, inner member (520) may be separable from outer member (518). In some such versions, a user may remove vacuum canister (500) from vacuum control module (400), remove lid portion (506), remove filter assembly (516), and replace the used inner member (520) with a new inner member (520). As yet another merely illustrative example, the user may replace lid portion (506) without replacing base portion (502). Other suitable arrangements and configurations for replacing vacuum canister (500), filter assembly (516), and/or inner member (520) to restore the ability of filter assembly (516) to communicate a vacuum will be apparent to those of ordinary skill in the art in view of the teachings herein.

Figure 13:
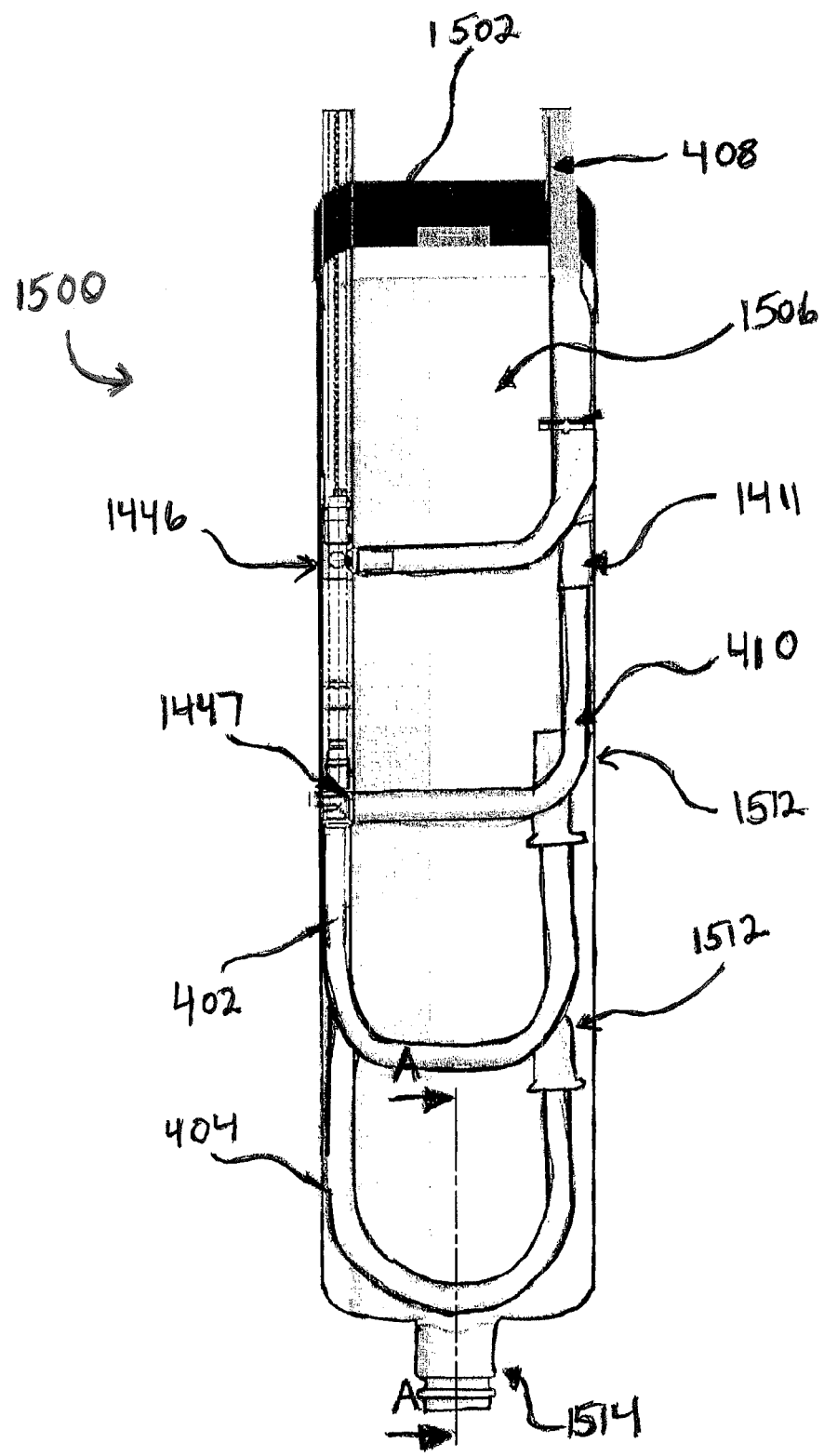
FIG. 13 depicts a top view of an alternate exemplary vacuum canister.
Figure 14:
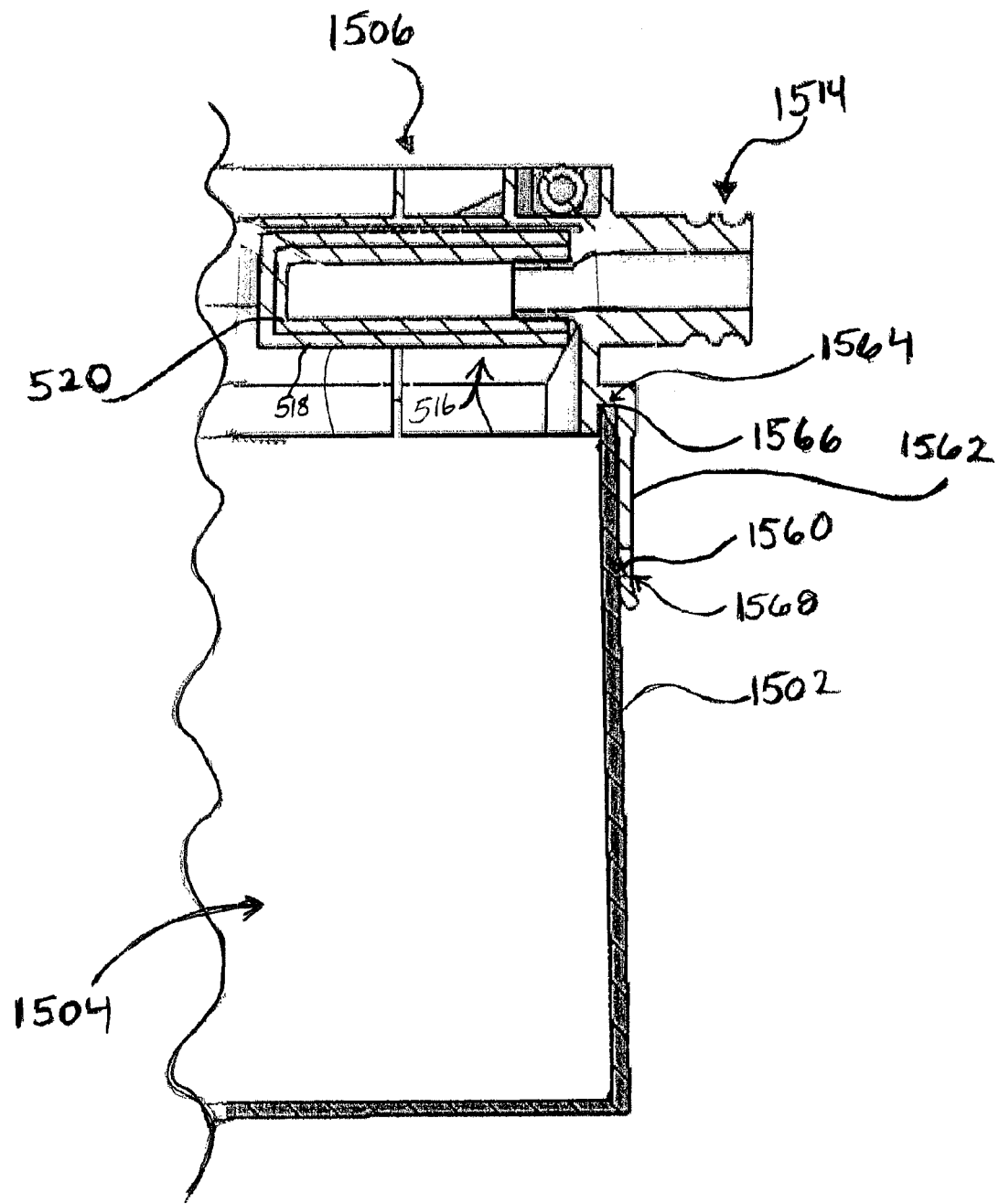
FIG. 14 depicts a partial cross-sectional view of the canister of FIG. 13, taken along section line A-A of FIG. 13.

FIGS. 13-14 depict an exemplary alternative version of a vacuum canister (1500) comprising an alternate base portion (1502) and an alternate lid portion (1506). As shown in FIG. 14, the vacuum canister (1500) may be used in conjunction with filter assembly (516) described above. In particular, lid portion (1506) provides an alternate tube connection and configuration, as discussed in more detail below. In addition, vacuum canister (1500) comprises an alternate engagement mechanism between base portion (1502) and lid portion (1506). In this example, base portion (1502) and lid portion (1506) are releasably engaged via a tab (1560) formed on the exterior surface of base portion (1502) and a resilient engagement member (1562) extending from lid portion (1506). As shown, lid portion (1506) comprises a slot (1564) configured to receive the upper end (1566) of base portion (1502). Tab (1560) of the present example does not extend about the full perimeter of base portion (1502), though it should be understood that tab (1560) may alternatively be formed as a ridge extending about the full perimeter of base portion (1502) or may have a variety of other configurations. Engagement member (1562) extends adjacent to base portion (1502) and includes a notch (1568) configured to releasably engage tab (1560). Engagement member (1562) and base portion (1502) may be configured to provide a snap-fit between notch (1568)

and tab (1560). A user may remove lid portion (1506) from base portion (1502) by disengaging tab (1560) from notch (1568) in engagement member (1560) and lifting lid portion (1506). After biopsy system (2) has been used, and liquid is present in reservoir (504), lid portion (1506) may be removed to gain access to reservoir (1504). A user may empty liquid from reservoir (1504) by pouring the liquid out of reservoir (1504) after removing lid portion (1506). Lid portion (1506) may then be re-engaged with base portion (1502) and continue using vacuum canister (1500).

The inventor contemplates that a variety of other configurations for vacuum canister (500) may be used, and that, like every other component of biopsy system (2) described herein, vacuum canister (500, 1500) need not be limited to the particular construction that is explicitly described herein. It is also contemplated that filter assembly (516) (and variations thereof) may be used in a variety of settings other than biopsy system (2), including but not limited to systems under vacuum, systems with pressurized fluids, and other types of systems. By way of example only, it should be understood that filter assembly (516) may be incorporated into an automobile fuel system to substantially prevent fuel flow in overturned vehicles. Various suitable ways in which filter assembly (516) may be incorporated into such other systems will be apparent to those of ordinary skill in the art in view of the teachings herein. Similarly, other types of systems in which filter system (516) may be incorporated will be apparent to those of ordinary skill in the art in view of the teachings herein.

B. Exemplary Tube Connection and Configuration

Figure 10:
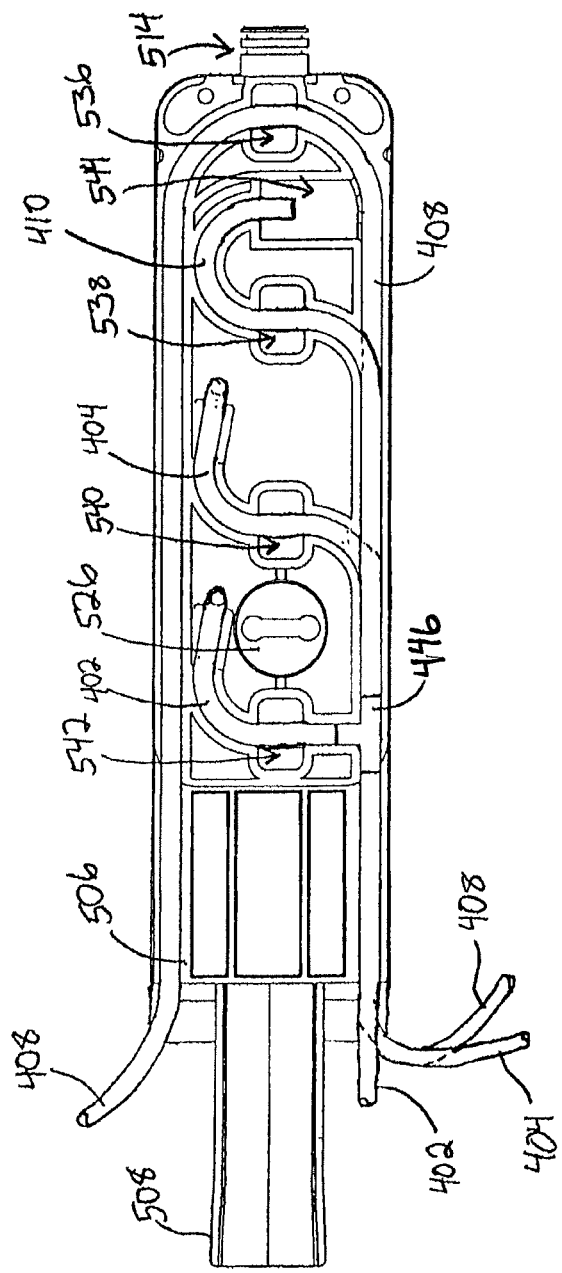
FIG. 10 depicts a top view of the vacuum canister of FIG. 6, with tubes engaged with a top portion of the canister.

FIG. 10 shows an example of tubes (402, 404, 408, 410) being provided in trenches (510) of canister (500). A plurality of top ports (512) are formed on lid portion (506), and each top port (512) is configured to have one of tubes (402, 404) coupled therewith. In particular, each top port (512) is configured to provide a path for fluid communication from a connected tube (402, 404) to the reservoir (504) defined by base portion (502).

As shown in FIG. 1, tube (408) is fed into tube (402). As shown in FIGS. 1 and 10, tube (410) is also fed into tube (402). In particular, a connector (446) connects vent tube (410) with tube (402); and a connector (448) connects saline tube (408) with tube (402). As shown, connector (446) is provided adjacent to canister (500), while connector (448) is provided near biopsy probe (102). In the present example, connectors (446, 448) simply provide a constantly open conduit between tubes (410, 402) and tubes (408, 402), respectively. In other versions, connectors (446, 448) may have any other suitable components (e.g., valve, etc.). It will be appreciated in view of the disclosure herein that the configuration of tubes (402, 408, 410) and connectors (446, 448) permits any of a vacuum, vent, or saline to be communicated through tube (402). An exemplary determination of which of these will be communicated through tube (402) will be described in greater detail below.

Alternate vacuum canister (1500), shown in FIG. 13, comprises lid portion (1506) that provides an alternate arrangement or configuration for tubes (402, 404, 408, 410). Similar to lid portion (506) described above, lid portion (1506) comprises a plurality of trenches (not shown), similar to trenches (510), that are configured to receive tubes (402, 404, 408, 410); and a plurality of recesses (not shown), similar to recesses (536, 538, 540, 542), that are configured to provide sufficient clearance for tips (472, 474, 476, 478) of solenoids (456) to fully engage tubes (402, 404, 408, 410). A plurality of top ports (1512) are formed on lid portion (1506). Top ports (1512) are substantially similar to top ports (512) described above, although top ports (1512) may be positioned differently than top ports (512). Each top port (1512) is configured have a respective one of tubes (402, 404) coupled therewith. In particular, each top port (1512) is configured to provide a path for fluid communication from a connected tube (402, 404) to the reservoir (1504) defined by base portion (1502). Accordingly, fluids (e.g., saline, blood, etc.) may be communicated from biopsy probe (102) during operation of biopsy device (100) and collected in reservoir (1504) of vacuum canister (1500). Lid portion (1506) further comprises a vacuum port (1514), which is substantially identical to vacuum port (514) described above.

The alternate tube configuration shown in FIG. 13 further includes a first connector (1446) and a second connector (1447). In particular, first connector (1446) connects saline tube (408) with tube (402) and second connector (1447) connects vent tube (410) with tube (402). In the present example, first connector (1446) and second connector (1447) simply provide a constantly open conduit between tubes (408, 402) and tubes (410, 402), respectively. In some other versions, first connector (1446) and second connector (1447) may have any other suitable components (e.g., valve, etc.). First connector (1446) and second connector (1447) may comprise t-junction connectors or any other suitable type of connector.

Vent tube (410) may terminate in an open end and vent into a recess, such as vent recess (544) shown in FIG. 10 and described above. Alternatively, vent tube (410) may terminate in a vent plug (1411) as shown in FIG. 13. Vent plug (1411) may be configured to allow air to freely flow through plug (1411) while simultaneously being able to substantially repel and/or absorb fluids attempting to enter or exit vent tube (410). In other words, vent plug (1411) may act as an inlet filter substantially preventing the flow of contaminants into canister (500, 1500). Various suitable components that may be used to form vent plug (1411), as well as various suitable forms that vent plug (1411) may take, will be apparent to those of ordinary skill in the art in view of the teachings herein. For instance, in some versions, vent plug (1411) comprises a layer formed of a hydrophobic material. Thus, any fluids that are incidentally communicated to the open end of vent tube (410) may be substantially repelled by the hydrophobic layer of vent plug (1411). Such a hydrophobic filter may also substantially prevent exterior contaminants from entering vent tube (410). In some other alternative versions, vent plug (1411) is substantially similar to filter assembly (516) described above, such that vent plug (1411) further comprises an outer layer formed by an occluding media. To the extent such fluids are able to pass through a hydrophobic inner layer of vent plug (1411), such fluids may be absorbed by the outer layer of vent plug (1411). Of course, vent plug (1411) may take a variety of other forms, and to the extent that a vent plug (1411) is even used, it should be understood that vent plug (1411) need not include a hydrophobic filter and/or occluding media. Other suitable configurations for vent plug (1411) will be apparent to those of ordinary skill in the art in view of the teachings herein. Alternatively, vent plug (1411) may simply be omitted if desired.

C. Exemplary Vacuum Control Module

Figure 15:
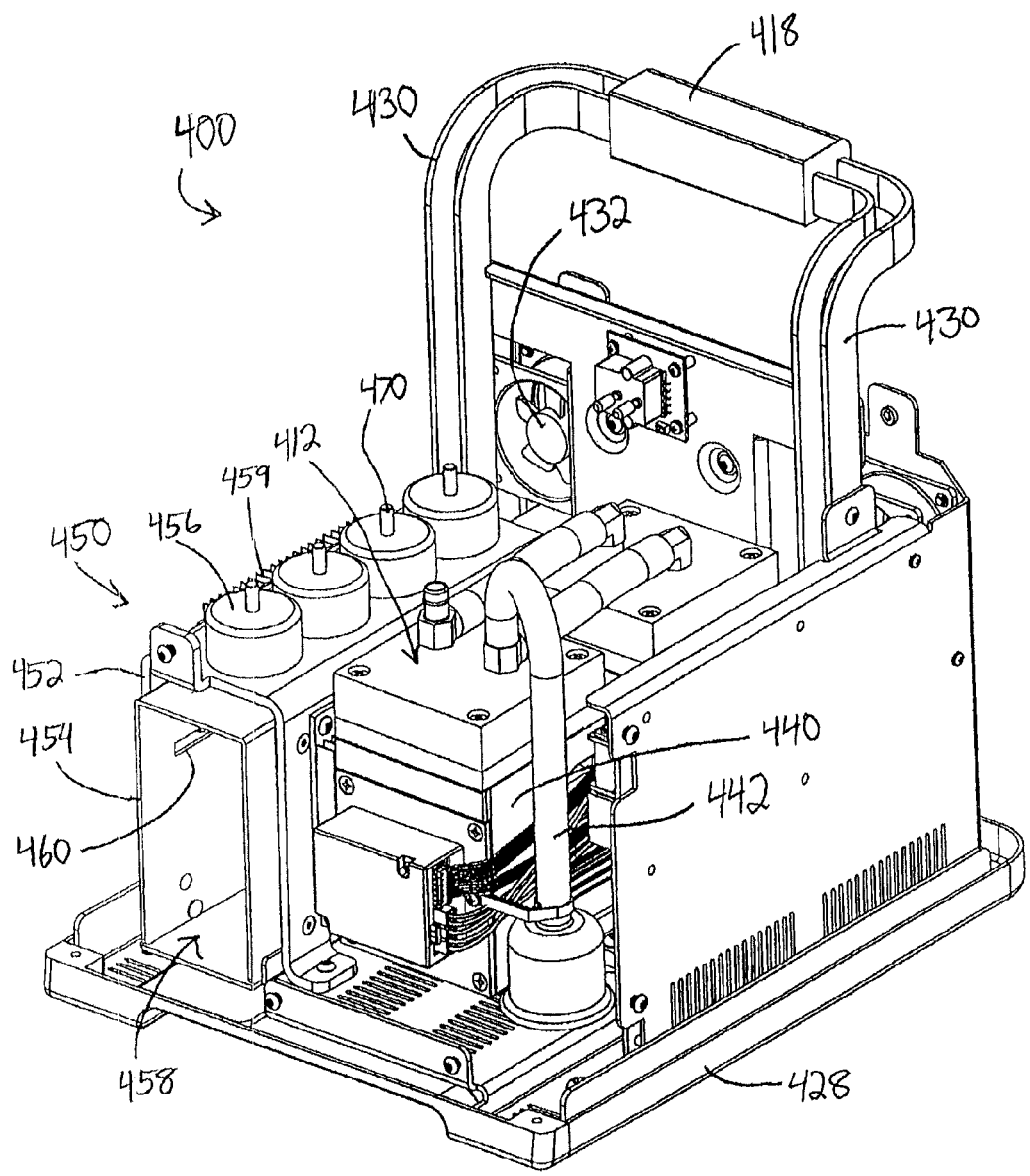
FIG. 15 depicts the vacuum control module of FIG. 6, with an outer casing removed.

As shown in FIGS. 6-7 and 15, the vacuum control module (400) of the present example comprises an outer casing (414), a vacuum canister slot (416), a handle portion (418), and a user interface (700). Outer casing (414) includes a face portion (420), behind which resides a display screen (702), capacitive switches (704), and a speaker (706). Face portion (420) is configured such that display screen (702) can be viewed therethrough; such that capacitive switches (704) may be activated therethrough; and such that sounds coming from speaker (706) can be heard therethrough. Display screen (702), switches (704), and speaker (706) may be regarded as collectively forming user interface (700). Outer casing (414) further comprises a top cover (422), a wraparound cover (424), and trim pieces (426). In some versions, vacuum control module (400) and associated components are configured and operable in accordance with the teachings of U.S. Pub. No. 2008/0228103, entitled "Vacuum Timing Algorithm for Biopsy Device," published Sep. 18, 2008, the disclosure of which is incorporated by reference herein.

Vacuum control module (400) of the present example may also include a plurality of ports which may be used to couple vacuum control module (400) to a variety of other devices. Examples of such ports are described in U.S. Pub. No. 2008/0228103, entitled "Vacuum Timing Algorithm for Biopsy Device," published Sep. 18, 2008, the disclosure of which is incorporated by reference herein. In some versions, a control module interface may be coupled between vacuum control module (400) and biopsy device (100). An exemplary control module interface is described in U.S. Non-Provisional patent application Ser. No. 12/337,814, entitled "Control Module Interface for MRI Biopsy Device," filed Dec. 18, 2008, the disclosure of which is incorporated by reference herein. In addition, vacuum control module (400) may include a cord socket for connecting vacuum control module (400) to an AC outlet using a conventional cord, and a power switch.

As shown in FIG. 15, a vacuum pump (440) is provided in vacuum control module (400). A muffler assembly (442) connected to vacuum pump (440) to reduce noise generated by vacuum pump (440). Vacuum pump (440) and muffler assembly (442) thus collectively provide a vacuum source (412) in the present example, though any other suitable components may be used. Vacuum pump (440) and muffler assembly (442) are fixedly secured relative to base portion (428), such as via screws, bolts, welds, or using other components or techniques. One or more rubber feet (not shown) or similar components may be positioned between vacuum pump (440) and base portion (428) to absorb vibration generated by vacuum pump, such as to further reduce noise. Other ways in which noise from vacuum pump (440) may be reduced will be apparent to those of ordinary skill in the art in view of the teachings herein.

In the present example, saline is provided for biopsy system (2) by a conventional saline bag (444), which is separate from vacuum control module (400). For instance, saline bag (444) may be coupled with tube (408) using any suitable conventional fitting. Alternate methods and configurations for incorporating and/or supplying saline are described in U.S. Pub. No. 2008/0228103, entitled "Vacuum Timing Algorithm for Biopsy Device," published Sep. 18, 2008, the disclosure of which is incorporated by reference herein. In some other versions, saline is not used at all with biopsy system (2). It will also be appreciated that vacuum control module (400) may also include a source of pressurized air, such as a pump or charged canister, etc. Such pressurized air may be communicated to a biopsy device (100) for any suitable purpose, including but not limited to communicating pressurized air through one or more lumens (20, 40, 52), activating a component (e.g., pneumatic motor or actuator, etc.) within biopsy device (100), or for any other purpose. Still other components that may be incorporated into or otherwise associated with vacuum control module (400) will be apparent to those of ordinary skill in the art in view of the teachings herein.

D. Exemplary Vacuum Canister Port in Control Module

Figure 16:
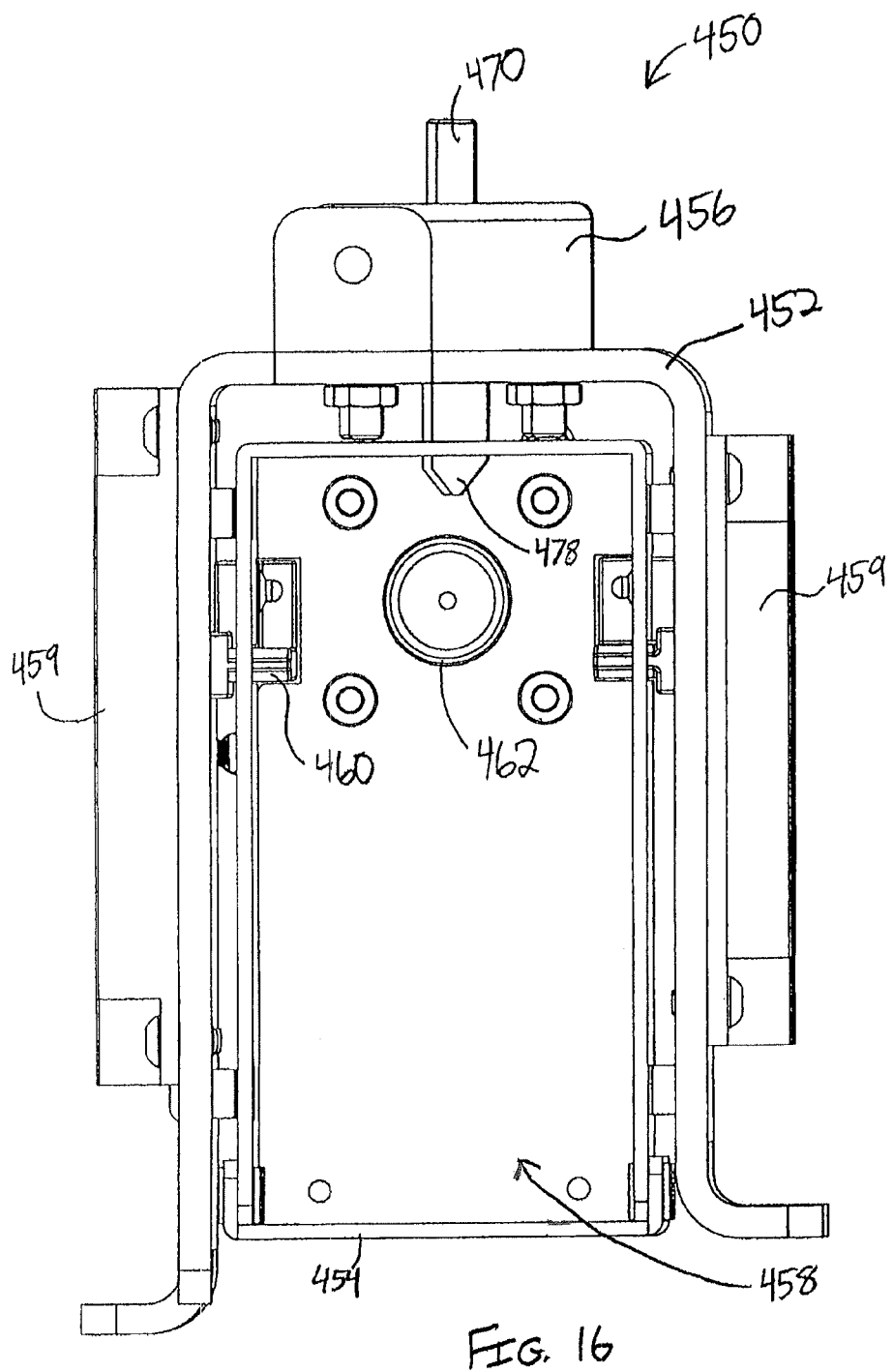
FIG. 16 depicts a front view of a vacuum canister port assembly of the vacuum control module of FIG. 6.

As shown in FIGS. 15-17, vacuum control module (400) of the present example further comprises a vacuum canister port assembly (450). Vacuum canister port assembly (450) comprises a bracket (452), an inner casing (454), and a plurality of solenoids (456). Bracket (452) is configured to be fixedly secured relative to base portion (428), such as via screws, bolts, welds, or using other components or techniques. Heat sinks (459) are secured to bracket (452), as are solenoids (456) and inner casing (454). Inner casing (454) defines a canister compartment (458), which is configured to receive vacuum canister (500, 1500). In some versions, vacuum canister port assembly (450) is configured and operable in accordance with the teachings of U.S. Pub. No. 2008/0228103, entitled "Vacuum Timing Algorithm for Biopsy Device," published Sep. 18, 2008, the disclosure of which is incorporated by reference herein.

E. Exemplary Vacuum Canister Quick-Connect

Inner casing (454) of the present example also includes a vacuum port (462). A port coupler (464) is provided on the exterior of inner casing (454), opposite to vacuum port (462), and is in fluid communication with vacuum port (462). Port coupler (464) is configured to be connected with a tube, hose, or other structure for fluidly coupling port coupler (464) with vacuum pump (440). In other words, vacuum pump (440) may be placed in fluid communication with vacuum port (462) via a tube (not shown) connected with port coupler (464), such that vacuum pump (440) may draw a vacuum through vacuum port (462). Vacuum port (462) is configured to engage with vacuum port (514, 1514) of vacuum canister (500, 1500) when vacuum canister (500, 1500) is inserted into canister compartment (458). In particular, vacuum port (462) provides a female-shaped complement to male-shaped vacuum port (514, 1514). O-rings (534) on vacuum port (514, 1514) are configured to provide sealed engagement between vacuum port (462) and vacuum port (514, 1514). Of course, the male-female arrangement between vacuum ports (462, 514, 1514) may be reversed, or some other relationship between vacuum ports (462, 514, 1514) may be provided. Furthermore, other variations may be used where o-rings (534) are substituted, supplemented, or omitted altogether.

F. Exemplary Pinching Valve System

Solenoids (456) each include a respective rod (470). Each rod (470) has a corresponding engagement tip (472, 474, 476, 478) secured unitarily thereto. Each solenoid (456) is operable to selectively move its rod (470) with tip (472, 474, 476, 478) upward or downward when solenoid (456) is activated, the upward or downward movement being dependent on the signal communicated to each solenoid (456). Rods (470) are positioned such that, when vacuum canister (500, 1500) is inserted in canister compartment (458), tips (472, 474, 476, 478) may be selectively engaged with tubes (402, 404, 408, 410) through selective activation of solenoids (456). In particular, when vacuum canister (500) is inserted into canister compartment (458) of vacuum control module (400), tip (472) is positioned to selectively engage saline tube (408), tip (474) is positioned to selectively engage vent tube (410), tip (476) is positioned to selectively engage axial vacuum tube (404), and tip (478) is positioned to selectively engage lateral vacuum tube (402). When vacuum canister (1500) is inserted into canister compartment (458) of vacuum control module (400), tip (472) is positioned to selectively engage axial vacuum tube (404), tip (474) is positioned to selectively engage lateral vacuum tube (402), tip (476) is positioned to selectively engage vent tube (410), and tip (478) is positioned to selectively engage saline tube (408). Of course, any other suitable arrangement or relationships may be used.

Recesses (536, 538, 540, 542) are formed in lid portion (506) of vacuum canister (500), and are configured to provide sufficient clearance for tips (472, 474, 476, 478) to fully engage tubes (402, 404, 408, 410). Such engagement may include tips (472, 474, 476, 478) pinching tubes (402, 404, 408, 410) against lid portion (506) (e.g., using lid portion (506) as an engagement surface), to thereby prevent fluid communication through tubes (402, 404, 408, 410). In the present example, recess (536) is configured to permit tip (472) to fully engage saline tube (408), recess (538) is configured to permit tip (474) to fully engage vent tube (410), recess (540) is configured to permit tip (476) to fully engage axial vacuum tube (404), and recess (542) is configured to permit tip (478) to fully engage lateral vacuum tube (402). Such full engagement of tips (472, 474, 476, 478) with tubes (402, 404, 408, 410) will serve to prevent fluid from being communicated through fully engaged tubes (402, 404, 408, 410) in this example. In other words, solenoids (456), rods (470), and tips (472, 474, 476, 478) may be used to serve a valving function with respect to tubes (402, 404, 408, 410), such that selective activation of solenoids (456) may permit or prevent communication of fluid through tubes (402, 404, 408, 410). Suitable combinations of permitting/preventing fluid communication through tubes (402, 404, 408, 410) during use of biopsy system (2) will be described in greater detail below. It should also be understood that lid portion (506) of vacuum canister (1500) may include similar recesses and provide the same type of pinching surface for tips (472, 474, 476, 478), thereby providing the same type of selective communication of fluid through tubes (402, 404, 408, 410).

Suitable configurations, features, and variations of solenoids (456) and associated components will be apparent to those of ordinary skill in the art in view of the teachings herein. For instance, solenoids (456) and associated components may be configured and operable in accordance with any of the teachings in U.S. Pub. No. 2008/0228103, entitled "Vacuum Timing Algorithm for Biopsy Device," published Sep. 18, 2008, the disclosure of which is incorporated by reference herein. Similarly, tubes (402, 404, 408, 410) may include longitudinal slits as described in U.S. Pub. No. 2008/0228103, entitled "Vacuum Timing Algorithm for Biopsy Device," published Sep. 18, 2008, the disclosure of which is incorporated by reference herein. Still other ways in which communication of fluid (e.g., saline, vacuum, venting, etc.), through tubes (402, 404, 408, 410) or otherwise within biopsy system (2), may be selectively controlled or provided will be apparent to those of ordinary skill in the art in view of the teachings herein.

G. Exemplary Motor Control

Vacuum control module (400) of the present example also includes a controller (480) operable to control motors (not shown) in holster (202) to drive the needle firing mechanism, the needle rotation mechanism, the cutter rotation and translation mechanism, and the tissue sample holder rotation mechanism. For instance, a single controller (480) may coordinate between motor functions on different motors that are within the same biopsy system (2). Vacuum control module (400) includes a port (482) for providing communication of motor control signals and power to the motors via a cable (484). In some other versions, motor control signals are provided wirelessly. Examples of suitable motors and associated characteristics and components are described in U.S. Pub. No. 2008/0228103, entitled "Vacuum Timing Algorithm for Biopsy Device," published Sep. 18, 2008, the disclosure of which is incorporated by reference herein. Other suitable motors will be apparent to those of ordinary skill in the art based on the teachings herein.

VI. Exemplary Modes of Operation

It will be appreciated in view of the disclosure herein that there are a variety of methods by which biopsy system (2) may be operated. For instance, regardless of the structures or techniques that are used to selectively control communication of fluid (e.g., saline, vacuum, venting, etc.), through tubes (402, 404, 408, 410) or otherwise within biopsy system (2), there are a variety of pneumatic timing algorithms that may be used. Such timing algorithms may vary based on an operational mode selected by a user. Furthermore, there may be overlap among operational modes (e.g., biopsy system (2) may be in more than one operational mode at a given moment, etc.). In addition to fluid communication timing algorithms being varied based on a selected mode of operation, other operational aspects of biopsy system (2) may vary based on a selected operational mode. For instance, operation of tissue sample holder (140) may vary based on a selected operational mode, as may operation of cutter (50) and other components of biopsy system (2). Several merely exemplary operational modes of operation that may be provided by biopsy system (2) are described in U.S. Pub. No. 2008/0228103, entitled "Vacuum Timing Algorithm for Biopsy Device," published Sep. 18, 2008, the disclosure of which is incorporated by reference herein, while others will be apparent to those of ordinary skill in the art in view of the teachings herein.

One exemplary operational mode is a sampling mode, during which a "sample" cycle may be initiated. This cycle is initiated after needle portion (10) has been inserted into the breast of a patient. With needle portion (10) inserted, lateral and axial vacuum are applied. In particular, solenoids (456) are activated such that tips (476, 478) are moved upward to substantially disengage tubes (402, 404), permitting a vacuum to be communicated through tubes (402, 404). Given the fluid connection of tube (402) with needle manifold (80), as well as the transverse openings (32) formed through wall (30), communication of a vacuum through tube (402) will draw a lateral vacuum relative to cannula lumen (20). Communication of a vacuum through tube (404) will draw an axial vacuum through cutter lumen (52), given the fluid connection of tube (404) to cutter lumen (52) via tissue sample holder (140) in this example. With the axial and lateral vacuum applied, cutter (50) is retracted axially. Such axial retraction is performed using cutter rotation and translation mechanism (120). The axial retraction of cutter (50) will serve to "open" aperture (16), which results in tissue prolapsing into aperture (16) under the influence of the above-described vacuums. Cutter (50) may dwell in a retracted position for a certain period of time to ensure sufficient prolapse of tissue.

Next, cutter (50) is advanced distally to sever tissue that is prolapsed through aperture (16). Such advancement may be accomplished using cutter rotation and translation mechanism (120). In some versions, vacuum lumen (40) is switched from vacuum to saline as cutter (50) advances. For instance, solenoids (456) may move tip (478) downward to pinch tube (402), thereby preventing further communication of vacuum through tube (402); and may move tip (472) upward to substantially disengage tube (408), thereby permitting communication of saline through tubes (408, 402). In some other versions, vacuum lumen (40) is switched from vacuum to vent as cutter (50) advances. For instance, solenoids (456) may move tip (478) downward to pinch tube (402), thereby preventing further communication of vacuum through tube (402); and may move tip (474) upward to substantially disengage tube (410), thereby permitting venting (e.g., into atmosphere) through tubes (408, 402). In some other versions, vacuum lumen (40) alternates between saline and venting. An axial vacuum continues to be communicated through cutter lumen (52) as cutter (50) is advanced.

As the distal end of cutter (50) passes the distal edge of aperture (16), such that cutter (50) "closes" aperture (16), the prolapsed tissue should be severed and at least initially contained within cutter lumen (52). Transverse openings (32) are configured such that at least one or more of transverse openings (32) are not covered by cutter (50) when cutter (50) has reached a position to "close" aperture (16). With aperture (16) closed and a vent being provided by transverse openings (32) through tube (402), an axial vacuum being communicated through cutter lumen (52) by tube (404) should draw the severed tissue sample proximally through cutter lumen (52) and into a chamber of tissue sample holder (140). The axial vacuum being communicated through cutter lumen (52) may also draw fluids (e.g. blood, saline, etc.) proximally through cutter lumen (52), through tissue sample holder (140) and, ultimately, into reservoir (504) of vacuum canister (500) via tube (404).

With the cutter (50) being completely advanced (e.g., such that all transverse openings (32) and aperture (16) are closed), and severed tissue sample being communicated proximally through cutter lumen (52) and into a chamber of tissue sample holder (140) by an axial vacuum drawn by tube (404), biopsy device (100) will be in a ready state. In this ready state, vacuum lumen (40) is vented to atmosphere, and axial vacuum tube (404) is sealed (a.k.a. "dead-headed"). In other words, tip (472) is pinching saline tube (408) to prevent fluid communication therethrough, tip (474) is substantially disengaged from vent tube (410) to permit venting to atmosphere therethrough, tip (476) is pinching axial vacuum tube (404) to prevent fluid communication therethrough, and tip (478) is pinching lateral vacuum tube (402) to prevent fluid communication therethrough. In this ready state, biopsy device (100) is ready to obtain another tissue sample, such as by initiating another sampling sequence as described above.

VII. Exemplary User Interface on Vacuum Control Module

Display screen (702), switches (704), and speaker (706) may be regarded as collectively forming user interface (700). In addition to or in lieu of a user interface (700) being provided by a vacuum control module (400), a user interface may be provided on biopsy device (100). To the extent that either or both of such user interfaces are provided, such user interfaces may be configured an operable in accordance with the teachings of U.S. Pub. No. 2008/0228103, entitled "Vacuum Timing Algorithm for Biopsy Device," published Sep. 18, 2008, the disclosure of which is incorporated by reference herein. Of course, other variations on user interface (704) and the corresponding screens, including alternative techniques, materials, and configurations, will be apparent to those of ordinary skill in the art in view of the teachings herein.

Embodiments of the present invention have application in conventional endoscopic and open surgical instrumentation as well as application in robotic-assisted surgery.

Embodiments of the devices disclosed herein can be designed to be disposed of after a single use, or they can be designed to be used multiple times. Embodiments may, in either or both cases, be reconditioned for reuse after at least one use. Reconditioning may include any combination of the steps of disassembly of the device, followed by cleaning or replacement of particular pieces, and subsequent reassembly. In particular, embodiments of the device may be disassembled, and any number of the particular pieces or parts of the device may be selectively replaced or removed in any combination. Upon cleaning and/or replacement of particular parts, embodiments of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, embodiments described herein may be processed before surgery. First, a new or used instrument may be obtained and if necessary cleaned. The instrument may then be sterilized. In one sterilization technique, the instrument is placed in a closed an sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a medical facility. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

What is claimed is:

1. A filter assembly comprising:
    (a) an outer member, wherein the outer member is configured to allow a vacuum to be communicated through the outer member, wherein the outer member comprises:
        (i) hydrophobic material, wherein the hydrophobic material is configured to substantially repel fluids at atmospheric pressure, and
        (ii) an interior cavity; and
    (b) an inner member, wherein at least a portion of the inner member is positioned within the interior cavity of the outer member, wherein the inner member comprises occluding media, wherein the occluding media is configured to absorb fluids both at atmospheric pressure and when a vacuum is being communicated through the inner member.

2. The filter assembly of claim 1, wherein the outer member comprises a cylindrical member.

3. The filter assembly of claim 1, wherein the inner member comprises a hollow, cylindrical member.

4. The filter assembly of claim 1, wherein the inner member comprises a cylindrical plug.

5. The filter assembly of claim 1, wherein the outer member has an open end and a closed end.

6. The filter assembly of claim 1, wherein the inner member has an open end and a closed end.

7. The filter assembly of claim 1, wherein the outer member is fixedly engaged with the inner member.

8. The filter assembly of claim 1, wherein the outer member is releasably engaged with the inner member.

9. The filter assembly of claim 1, further comprising a vacuum canister defining a reservoir and a first fluid port in communication with the reservoir, wherein the open end of the inner member is engaged with the first fluid port of the vacuum canister.

10. The filter assembly of claim 9, further comprising a vacuum control module, wherein the vacuum control module comprises a vacuum pump and a second fluid port in communication with the vacuum pump, wherein the second fluid port is fluidly coupled with the first fluid port.

11. A filter assembly for a biopsy device, the filter assembly comprising:
(a) a primary barrier, wherein the primary barrier comprises:
(i) an inner surface,
(ii) an outer surface, and
(iii) hydrophobic material configured to allow a vacuum to be communicated through the primary barrier, wherein the hydrophobic material is further configured to substantially prevent fluids from passing through the primary barrier at atmospheric pressure; and
(b) a secondary barrier adjacent to the primary barrier, wherein the secondary barrier comprises:
(i) an inner surface, wherein the inner surface of the secondary barrier defines an interior cavity,
(ii) an outer surface, and
(iii) occluding media configured to allow a vacuum to be communicated through the secondary barrier, wherein the occluding media is further configured to absorb fluids that pass through the primary barrier.

12. The filter assembly of claim 11, wherein the outer surface of the secondary barrier abuts the inner surface of the primary barrier.

13. The filter assembly of claim 11, wherein the inner surface of the primary barrier defines a primary interior cylindrical cavity.

14. The filter assembly of claim 13, wherein the primary interior cylindrical cavity is sized and shaped to receive at least a portion of the secondary barrier.

15. The filter assembly of claim 11, wherein the primary barrier and the secondary barrier are sintered together.

16. A vacuum canister for a biopsy device comprising:
(a) a base portion, wherein the base portion defines a reservoir configured to collect fluids;
(b) a filter assembly, wherein the filter assembly is in fluid communication with the reservoir of the base portion, wherein the filter assembly comprises:
(i) an outer hollow cylindrical member, wherein the outer hollow cylindrical member is formed at least in part of a hydrophobic material, and
(ii) an inner hollow cylindrical member, wherein the inner hollow cylindrical member is formed at least in part of a fluid absorbent material, wherein at least a portion of the inner hollow cylindrical member is positioned within the outer hollow cylindrical member, wherein the inner hollow cylindrical member presents an inner surface;
(c) a vacuum port;
(d) a conduit, wherein the conduit extends between the vacuum port and the reservoir to provide fluid communication between the vacuum port and the reservoir; and
(e) an attachment member, wherein the attachment member extends substantially circumferentially about a first end of the conduit, wherein the attachment member engages the inner surface of the inner hollow cylindrical member, wherein the filter assembly is in fluid communication with the conduit through the attachment member.

17. The vacuum canister of claim 16, wherein the vacuum port extends outwardly relative to the base portion.

18. The vacuum canister of claim 16, further comprising a lid coupled with the base portion, wherein the filter assembly is secured to the lid.

19. The vacuum canister of claim 18, wherein the lid is removably coupled with the base portion through a snap fitting.

20. The vacuum canister of claim 18, further comprising a plurality of tubes coupled with the lid, wherein the lid provides fluid communication between the reservoir and at least some of the tubes.

* * * * *